United States Patent
Hernandez

(10) Patent No.: US 10,390,943 B2
(45) Date of Patent: Aug. 27, 2019

(54) DOUBLE ORIFICE DEVICE FOR TRANSCATHETER MITRAL VALVE REPLACEMENT

(71) Applicant: Evalve, Inc., Santa Clara, CA (US)

(72) Inventor: Carlos G. Hernandez, San Francisco, CA (US)

(73) Assignee: EVALVE, INC., Santa Clara, CA (US)

( * ) Notice: Subject to any disclaimer, the term of this patent is extended or adjusted under 35 U.S.C. 154(b) by 533 days.

(21) Appl. No.: 14/216,813

(22) Filed: Mar. 17, 2014

(65) Prior Publication Data

US 2015/0257877 A1    Sep. 17, 2015

(51) Int. Cl.
*A61F 2/24* (2006.01)
*A61B 17/04* (2006.01)
(Continued)

(52) U.S. Cl.
CPC ........ *A61F 2/2409* (2013.01); *A61B 17/0401* (2013.01); *A61B 17/08* (2013.01); *A61F 2/2403* (2013.01); *A61F 2/2436* (2013.01); *A61F 2/2463* (2013.01); *A61F 2/2466* (2013.01); *A61B 17/3478* (2013.01);
(Continued)

(58) Field of Classification Search
CPC .... A61F 2/2409; A61F 2/2463; A61F 2/2466; A61F 2/2436; A61F 2/2403; A61F 2/2427; A61F 2/2442; A61F 2/2445; A61B 17/0401; A61B 2017/00783; A61B 2017/081
See application file for complete search history.

(56) References Cited

U.S. PATENT DOCUMENTS 1,996,261 A    4/1935   Storz
2,097,018 A    10/1937  Chamberlain
(Continued)

FOREIGN PATENT DOCUMENTS

DE    3504292     7/1986
DE    10116168    11/2001
(Continued)

OTHER PUBLICATIONS

U.S. Appl. No. 14/216,787, Apr. 8, 2016, Office Action.
(Continued)

*Primary Examiner* — Kathleen S Holwerda
(74) *Attorney, Agent, or Firm* — Baker Botts L.L.P.

(57) ABSTRACT

Valve devices for replacement of mitral valves while preserving valvular and subvalvular mitral valve apparatus. The valve device may be configured as a double orifice valve replacement device, and may include an anchoring and manifold assembly coupleable to a delivery catheter. The assembly may include means for anchoring the device to the mitral valve or to a fixation device already attached to the mitral valve. A peripheral ring anchoring system secured to the assembly may include at least one expandable anchoring ring that is expandable within an orifice of the mitral valve so as to surround the orifice perimeter. A helical suture may be helically disposable about the ring, securing the ring to adjacent leaflet tissue. A trap door valve including a trap door body that seals against the anchoring ring during systole and unseals during the diastolic portion of the cardiac cycle may be provided.

19 Claims, 22 Drawing Sheets

(51) Int. Cl.
  *A61B 17/08* (2006.01)
  *A61B 17/34* (2006.01)
  *A61B 17/00* (2006.01)
  *A61B 90/00* (2016.01)

(52) U.S. Cl.
  CPC ............... *A61B 2017/00243* (2013.01); *A61B 2017/00783* (2013.01); *A61B 2017/081* (2013.01); *A61B 2090/3908* (2016.02); *A61B 2090/3925* (2016.02); *A61F 2220/0091* (2013.01); *A61F 2230/001* (2013.01); *A61F 2230/0067* (2013.01)

(56) References Cited

U.S. PATENT DOCUMENTS

| | | |
|---|---|---|
| 2,108,206 A | 2/1938 | Meeker |
| 3,296,668 A | 1/1967 | Aiken |
| 3,378,010 A | 4/1968 | Codling et al. |
| 3,557,780 A | 1/1971 | Sato |
| 3,671,979 A | 6/1972 | Moulopoulos |
| 3,675,639 A | 7/1972 | Cimber |
| 3,874,338 A | 4/1975 | Happel |
| 4,007,743 A | 2/1977 | Blake |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,458,682 A | 7/1984 | Cerwin |
| 4,425,908 A | 11/1984 | Simon |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,878,495 A | 11/1989 | Grayzel |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,108,368 A | 4/1992 | Hammerslag et al. |
| 5,125,758 A | 6/1992 | DeWan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,201,757 A | 4/1993 | Heyn et al. |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Krauter et al. |
| 5,364,351 A | 11/1994 | Heinzelman et al. |
| 5,368,564 A | 11/1994 | Savage |
| 5,368,601 A | 11/1994 | Sauer et al. |
| 5,383,886 A | 1/1995 | Kensey et al. |
| 5,391,182 A | 2/1995 | Chin |
| 5,403,312 A | 4/1995 | Yates et al. |
| 5,403,326 A | 4/1995 | Harrison et al. |
| 5,411,552 A | 5/1995 | Andersen et al. |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,445,646 A | 8/1995 | Euteneuer et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |
| 5,569,274 A | 10/1996 | Rapacki et al. |
| 5,571,085 A | 11/1996 | Accisano, III |
| 5,571,135 A | 11/1996 | Fraser et al. |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup, III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |
| 5,620,461 A | 4/1997 | Muijs Van De Moer et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keital et al. |

(56) References Cited

U.S. PATENT DOCUMENTS

| | | |
|---|---|---|
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,749,828 A | 5/1998 | Solomon et al. |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,614 A | 1/1999 | Stevens et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,280 A | 11/1999 | Euteneuer et al. |
| 5,989,284 A | 11/1999 | Laufer |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,143,024 A | 11/2000 | Campbell et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,168,617 B1 | 1/2001 | Blaeser et al. |
| 6,171,320 B1 | 1/2001 | Monassevitch |
| 6,174,322 B1 | 1/2001 | Schneidt |
| 6,182,664 B1 | 2/2001 | Cosgrove |
| 6,187,003 B1 | 2/2001 | Buysse et al. |
| 6,190,408 B1 | 2/2001 | Melvin |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,579,279 B1 | 6/2003 | Rabiner et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |

(56) References Cited

U.S. PATENT DOCUMENTS

| | | |
|---|---|---|
| 6,702,825 B2 | 3/2004 | Frazier et al. |
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,033,390 B2 | 4/2006 | Johnson et al. |
| 7,048,754 B2 | 5/2006 | Martin et al. |
| 7,112,207 B2 | 9/2006 | Allen et al. |
| 7,226,467 B2 | 6/2007 | Lucatero et al. |
| 7,288,097 B2 | 10/2007 | Seguin |
| 7,291,168 B2 | 11/2007 | Macoviak et al. |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 8,070,799 B2 | 12/2011 | Righini et al. |
| 8,518,106 B2 | 8/2013 | Duffy et al. |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0173811 A1 | 11/2002 | Tu et al. |
| 2002/0173841 A1* | 11/2002 | Ortiz ............ A61F 2/2409 623/2.11 |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0199975 A1 | 10/2003 | Gabbay |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0015232 A1* | 1/2004 | Shu ............ A61F 2/2409 623/2.4 |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092858 A1 | 5/2004 | Wilson et al. |
| 2004/0092962 A1 | 5/2004 | Thornton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |

(56) References Cited

U.S. PATENT DOCUMENTS

| | | |
|---|---|---|
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0038509 A1 | 2/2005 | Ashe |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0060030 A1 | 3/2005 | Lashinski et al. |
| 2005/0070844 A1 | 3/2005 | Chow et al. |
| 2005/0149014 A1 | 7/2005 | Hauck et al. |
| 2005/0159810 A1 | 7/2005 | Filsoufi |
| 2005/0182475 A1 | 8/2005 | Jen et al. |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0272975 A1 | 12/2005 | McWeeney et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0015179 A1 | 1/2006 | Bulman-Fleming et al. |
| 2006/0020275 A1 | 1/2006 | Goldfarb et al. |
| 2006/0020327 A1* | 1/2006 | Lashinski ............ A61F 2/2436 623/1.25 |
| 2006/0030866 A1 | 2/2006 | Schreck |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Randert et al. |
| 2006/0252993 A1 | 11/2006 | Freed et al. |
| 2007/0038293 A1 | 2/2007 | St. Goar et al. |
| 2007/0055289 A1 | 3/2007 | Scouten et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0197858 A1 | 8/2007 | Goldfarb et al. |
| 2007/0198082 A1 | 8/2007 | Kapadia et al. |
| 2007/0213812 A1 | 9/2007 | Webler et al. |
| 2008/0039935 A1 | 2/2008 | Buch et al. |
| 2008/0051703 A1 | 2/2008 | Thorton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goar et al. |
| 2008/0171976 A1 | 7/2008 | Rios et al. |
| 2008/0183194 A1 | 7/2008 | Goldfarb et al. |
| 2008/0195126 A1 | 8/2008 | Solem |
| 2008/0294175 A1 | 11/2008 | Bardsley et al. |
| 2009/0156995 A1 | 6/2009 | Martin et al. |
| 2009/0157162 A1 | 6/2009 | Chow et al. |
| 2009/0163934 A1 | 6/2009 | Raschdorf, Jr. et al. |
| 2009/0163986 A1 | 6/2009 | Tieu et al. |
| 2009/0177266 A1 | 7/2009 | Powell et al. |
| 2009/0182200 A1 | 7/2009 | Golden et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goar et al. |
| 2010/0121437 A1 | 5/2010 | Subramanian et al. |
| 2010/0262231 A1 | 10/2010 | Tuval et al. |
| 2010/0268204 A1 | 10/2010 | Tieu et al. |
| 2010/0298929 A1 | 11/2010 | Thornton et al. |
| 2012/0179184 A1 | 7/2012 | Orlov |
| 2012/0265222 A1* | 10/2012 | Gordin ............ A61B 17/06166 606/148 |
| 2013/0066341 A1 | 3/2013 | Ketai et al. |
| 2013/0066342 A1 | 3/2013 | Dell et al. |
| 2013/0190772 A1 | 7/2013 | Doerr |
| 2013/0231735 A1 | 9/2013 | Deem et al. |
| 2013/0304181 A1 | 11/2013 | Green et al. |
| 2013/0304200 A1 | 11/2013 | McLean et al. |
| 2014/0039511 A1 | 2/2014 | Morris et al. |
| 2014/0180124 A1 | 6/2014 | Whiseant et al. |
| 2014/0200649 A1 | 7/2014 | Essinger et al. |
| 2014/0276913 A1 | 9/2014 | Tah et al. |
| 2014/0277356 A1 | 9/2014 | Shumer et al. |
| 2014/0309661 A1 | 10/2014 | Sheps et al. |
| 2014/0309670 A1 | 10/2014 | Bakos et al. |
| 2014/0350662 A1 | 11/2014 | Vaturi |
| 2014/0358224 A1 | 12/2014 | Tegels et al. |
| 2015/0051698 A1 | 2/2015 | Ruyra Baliarda et al. |
| 2015/0094800 A1 | 4/2015 | Chawla |
| 2015/0119981 A1 | 4/2015 | Khairkhahan et al. |
| 2015/0142100 A1 | 5/2015 | Morriss et al. |
| 2015/0230947 A1 | 8/2015 | Krieger et al. |
| 2015/0366665 A1 | 12/2015 | Lombardi et al. |
| 2016/0015410 A1 | 1/2016 | Asirvatham et al. |
| 2016/0038280 A1 | 2/2016 | Morriss et al. |
| 2016/0045314 A1 | 2/2016 | Keren et al. |
| 2016/0051386 A1 | 2/2016 | Haarmann-Thiemann |
| 2016/0116056 A1 | 4/2016 | Geissler |
| 2016/0128767 A1 | 5/2016 | Azamian et al. |
| 2016/0174979 A1 | 6/2016 | Wei |
| 2017/0143330 A1 | 5/2017 | Basude et al. |
| 2018/0008268 A1 | 1/2018 | Khairkhahan |
| 2018/0036119 A1 | 2/2018 | Wei et al. |
| 2018/0125658 A1 | 5/2018 | Prabhu |
| 2018/0133007 A1 | 5/2018 | Prabhu |
| 2018/0161159 A1 | 6/2018 | Lee et al. |

FOREIGN PATENT DOCUMENTS

| | | |
|---|---|---|
| EP | 0179562 | 7/1989 |
| EP | 0558031 | 2/1993 |
| EP | 0684012 | 11/1995 |
| EP | 0727239 | 8/1996 |
| EP | 0782836 | 7/1997 |
| EP | 1230899 | 8/2002 |
| EP | 1674040 | 6/2006 |
| EP | 1935377 | 6/2008 |
| EP | 2005912 | 12/2008 |
| EP | 2641570 | 9/2013 |
| FR | 2768324 | 3/1999 |
| GB | 1598111 | 9/1981 |
| GB | 2151142 | 7/1985 |
| JP | H09253030 | 9/1997 |
| JP | H11089937 | 4/1999 |
| JP | 2000283130 | 10/2000 |
| JP | 2015502548 | 1/2015 |
| WO | WO1981000668 | 3/1981 |
| WO | WO 91/01689 | 2/1991 |
| WO | WO1991018881 | 12/1991 |
| WO | WO1992012690 | 8/1992 |
| WO | WO1994018881 | 9/1994 |
| WO | WO1994018893 | 9/1994 |
| WO | WO1995011620 | 5/1995 |
| WO | WO1995015715 | 6/1995 |
| WO | WO1996014032 | 5/1996 |
| WO | WO1996020655 | 7/1996 |
| WO | WO1996022735 | 8/1996 |
| WO | WO1996030072 | 10/1996 |
| WO | WO1997018746 | 5/1997 |

(56) References Cited

FOREIGN PATENT DOCUMENTS

| | | |
|---|---|---|
| WO | WO1997025927 | 7/1997 |
| WO | WO1997026034 | 7/1997 |
| WO | WO1997038748 | 10/1997 |
| WO | WO1997039688 | 10/1997 |
| WO | WO1997048436 | 12/1997 |
| WO | WO1998007375 | 2/1998 |
| WO | WO1998024372 | 6/1998 |
| WO | WO1998030153 | 7/1998 |
| WO | WO1998032382 | 7/1998 |
| WO | WO 98/35638 | 8/1998 |
| WO | WO 99/00059 | 1/1999 |
| WO | WO 99/01377 | 1/1999 |
| WO | WO1999007354 | 2/1999 |
| WO | WO1999013777 | 3/1999 |
| WO | WO 99/44524 | 9/1999 |
| WO | WO1999066967 | 12/1999 |
| WO | WO 00/03759 | 1/2000 |
| WO | WO2000002489 | 1/2000 |
| WO | WO2000003651 | 1/2000 |
| WO | WO2000012168 | 3/2000 |
| WO | WO2000044313 | 8/2000 |
| WO | WO 00/60995 | 10/2000 |
| WO | WO2000059382 | 10/2000 |
| WO | WO2001000111 | 1/2001 |
| WO | WO2001000114 | 1/2001 |
| WO | WO2001003651 | 1/2001 |
| WO | WO2001026557 | 4/2001 |
| WO | WO2001026586 | 4/2001 |
| WO | WO2001026587 | 4/2001 |
| WO | WO2001026588 | 4/2001 |
| WO | WO2001026703 | 4/2001 |
| WO | WO2001028455 | 4/2001 |
| WO | WO2001047438 | 7/2001 |
| WO | WO2001049213 | 7/2001 |
| WO | WO2001050985 | 7/2001 |
| WO | WO2001054618 | 8/2001 |
| WO | WO2001056512 | 8/2001 |
| WO | WO2001066001 | 9/2001 |
| WO | WO2001070320 | 9/2001 |
| WO | WO2001089440 | 11/2001 |
| WO | WO2001095831 | 12/2001 |
| WO | WO2001095832 | 12/2001 |
| WO | WO2001097741 | 12/2001 |
| WO | WO2002000099 | 1/2002 |
| WO | WO2002001999 | 1/2002 |
| WO | WO2002003892 | 1/2002 |
| WO | WO2002034167 | 5/2002 |
| WO | WO2002060352 | 8/2002 |
| WO | WO2002062263 | 8/2002 |
| WO | WO2002062270 | 8/2002 |
| WO | WO2002062408 | 8/2002 |
| WO | WO2003001893 | 1/2003 |
| WO | WO2003003930 | 1/2003 |
| WO | WO2003020179 | 3/2003 |
| WO | WO2003028558 | 4/2003 |
| WO | WO2003037171 | 5/2003 |
| WO | WO2003047467 | 6/2003 |
| WO | WO2003049619 | 6/2003 |
| WO | WO2003073910 | 9/2003 |
| WO | WO2003073913 | 9/2003 |
| WO | WO2003082129 | 10/2003 |
| WO | WO2003094801 | 11/2003 |
| WO | WO2003105667 | 12/2003 |
| WO | WO 04/006810 | 1/2004 |
| WO | WO2004004607 | 1/2004 |
| WO | WO2004012583 | 2/2004 |
| WO | WO2004012789 | 2/2004 |
| WO | WO2004014282 | 2/2004 |
| WO | WO2004019811 | 3/2004 |
| WO | WO2004030570 | 4/2004 |
| WO | WO2004037317 | 5/2004 |
| WO | WO2004045370 | 6/2004 |
| WO | WO2004045378 | 6/2004 |
| WO | WO2004045463 | 6/2004 |
| WO | WO2004047679 | 6/2004 |
| WO | WO2004062725 | 7/2004 |
| WO | WO2004082523 | 9/2004 |
| WO | WO2004082538 | 9/2004 |
| WO | WO2004093730 | 11/2004 |
| WO | WO 04/103162 | 12/2004 |
| WO | WO2004112585 | 12/2004 |
| WO | WO2004112651 | 12/2004 |
| WO | WO2005002424 | 1/2005 |
| WO | WO2005018507 | 3/2005 |
| WO | WO2005027797 | 3/2005 |
| WO | WO2005032421 | 4/2005 |
| WO | WO2005062931 | 7/2005 |
| WO | WO2005112792 | 12/2005 |
| WO | WO2006037073 | 4/2006 |
| WO | WO 06/113906 | 10/2006 |
| WO | WO2006105008 | 10/2006 |
| WO | WO2006105009 | 10/2006 |
| WO | WO2006115875 | 11/2006 |
| WO | WO2006115876 | 11/2006 |
| WO | WO2011102968 | 8/2011 |
| WO | WO 2013/049734 | 4/2013 |
| WO | WO 2013/103934 | 7/2013 |
| WO | WO2015020971 | 2/2015 |
| WO | WO2018026445 | 2/2018 |
| WO | WO2018089617 | 5/2018 |
| WO | WO2018094042 | 5/2018 |

OTHER PUBLICATIONS

U.S. Appl. No. 14/216,787, filed Mar. 17, 2014, Basude et al.
Abe et al, De Vega's Annuloplasty for Acquired Tricuspid Disease: Early and Late Results in 110 Patients, Ann. Thorac. Surg., Jan. 1989, pp. 670-676, vol. 48.
Ali Khan et al, Blade Atrial Septostomy: Experience with the First 50 Procedures, Cathet. Cardiovasc. Diagn., Aug. 1991, pp. 257-262, vol. 23.
Alvarez et al, Repairing the Degenerative Mitral Valve: Ten to Fifteen-year Follow-up, J. Thorac. Cardiovasc. Surg., Aug. 1996, pp. 238-247, vol. 112.
Bach et al, Early Improvement in Congestive Heart Failure After Correction of Secondary Mitral Regurgitation in End-stage Cardiomyopathy, Am. Heart J., Jun. 1995, pp. 1165-1170, vol. 129.
Bach et al, Improvement Following Correction of Secondary Mitral Regurgitation in End-stage Cardiomyopathy With Mitral Annuloplasty, Am. J. Cardiol., Oct. 15, 1996, pp. 966-969, vol. 78.
Bolling et al, Surgery for Acquired Heart Disease: Early Outcome of Mitral Valve Reconstruction in Patients with End-stage Cardiomyopathy, J. Thor. and Cariovasc. Surg., Apr. 1995, pp. 676-683, vol. 109.
Dec et al, Idiopathic Dilated Cardiomyopathy, N. Engl. J. Med., Dec. 8, 1994, pp. 1564-1575, vol. 331.
Fucci et al, Improved Results with Mitral Valve Repair Using New Surgical Techniques, Eur. J. Cardiothorac. Surg., Nov. 1995, pp. 621-627, vol. 9.
Kameda et al, Annuloplasty for Severe Mitral Regurgitation Due to Dilated Cardiomyopathy, Ann. Thorac. Surg., 1996, pp. 1829-1832, vol. 61.
Maisano et al, The Edge-to-edge Technique: A Simplified Method to Correct Mitral Insufficiency, Eur. J. Cardiothorac. Surg., Jan. 14, 1998, pp. 240-246, vol. 13.
McCarthy et al, Tricuspid Valve Repair with the Cosgrove-Edwards Annuloplasty System, Ann. Thorac. Surg., Jan. 16, 1997, pp. 267-268, vol. 64.
Park et al, Clinical Use of Blade Atrial Septostomy, Circulation, 1978, pp. 600-608, vol. 58.
Ricchi et al, Linear Segmental Annuloplasty for Mitral Valve Repair, Ann. Thorac. Surg., Jan. 7, 1997, pp. 1805-1806, vol. 63.
Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.
Uchida et al, Percutaneous Cardiomyotomy and Valvulotomy with Angioscopic Guidance, Am. Heart J., Apr. 1991, pp. 1221-1224, vol. 121.

(56) References Cited

OTHER PUBLICATIONS

Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.
U.S. Appl. No. 14/216,787, Nov. 7, 2016, Notice of Allowance.
U.S. Appl. No. 15/724,545, filed Oct. 4, 2017, Prabhu.
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The edge to edge technique," The European Association for Cardio-Thoracic Surgery 14th Annual Meeting, Oct. 7-11, 2000, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Arisi et al., "Mitral Valve Repair with Alfieri Technique in Mitral Regurgitation of Diverse Etiology: Early Echocardiographic Results," Circulation Supplement II, 104(17):3240 (2001).
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only], 2004.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action issued in Chinese Application No. 200980158707.2 dated Sep. 9, 2013.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., #62 Early Clinical Experience with an Implantable, Intracardiac Circulatory Support Device: Operative Considerations and Physiologic Implications, 2003 STS Presentation, 1 page total. [Abstract Only].

Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene, "Early and postoperative results results of metal and tricuspid valve insufficiency surgical treatment using edge-to-edge central coaptation procedure," (Oct. 2002) 38 (Suppl 2):172-175.
Gatti et al., "The edge to edge technique as a trick to rescue an imperfect mitral valve repair," Eur. J. Cardiothorac Surg, 22:817-820 (2002).
Gillinov et al., "Is Minimally Invasive Heart Valve Surgery a Paradigm for the Future?" Current Cardiology Reports, 1:318-322 (1999).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion of PCT Application No. PCT/US2009/068023, dated Mar. 2, 2010, 10 pages total.
Izzat et al., "Early Experience with Partial Left Ventriculectomy in the Asia-Pacific Region," Annals of Thoracic Surgery, 67:1703-1707 (1999).
Kallner et al., "Transaortic Approach for the Alfieri Stitch," Ann Thorac Surg, 71:378-380 (2001).
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Kherani et al., "The Edge-To-Edge Mitral Valve Repair: The Columbia Presbyterian Experience," Ann. Thorac. Surg., 78:73-76 (2004).
Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).
Maisano et al., "The double orifice repair for Barlow Disease: a simple solution for a complex repair," Supplement I Circulation, (Nov. 1999); 100(18):1-94.
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).

(56) References Cited

OTHER PUBLICATIONS

McCarthy et al., "Partial left ventriculectomy and mitral valve repair for end-stage congestive heart failure," European Journal of Cardio-thoracic Surgery, 13:337-343 (1998).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al., "Tricuspid Valve Incompetence Caused by Nonpenetrating Thoracic Trauma", Annals of Thoracic Surgery, 51:320-322 (1991).
Osawa et al., "Partial Left Ventriculectomy in a 3-Year Old Boy with Dilated Cardiomyopathy," Japanese Journal of Thoracic and Cardiovascular Surg, 48:590-593 (2000).
Patel et al., #57 Epicardial Atrial Defibrillation: Novel Treatment of Postoperative Atrial Fibrillation, 2003 STS Presentation, [Abstract Only].
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Robicsek et al., #60 The Bicuspid Aortic Valve: How Does It Function? Why Does It Fail? 2003 STS Presentation, [Abstract Only].
Supplemental European Search Report of EP Application No. 02746781, dated May 13, 2008, 3 pages total.
Supplementary European Search Report issued in European Application No. 05753261.6 dated Jun. 9, 2011, 3 pages total.
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., #59 Annular Geometric Remodeling in Chronic Ischemic Mitral Regurgitation, 2003 STS Presentation, [Abstract Only].
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
Umana et al., "'Bow-tie' Mitral Valve Repair Successfully Addresses Subvalvular Dysfunction in Ischemic Mitral Regurgitation," Surgical Forum, XLVIII:279-280 (1997).
Votta et al., "3-D Computational Analysis of the Stress Distribution on the Leaflets after Edge-to-Edge Repair of Mitral Regurgitation," Journal of Heart Valve Disease, 11:810-822 (2002).
U.S. Appl. No. 14/577,852, Oct. 20, 2016, Office Action.
U.S. Appl. No. 14/577,852, May 16, 2017, Office Action.
U.S. Appl. No. 14/577,852, Sep. 7, 2017, Office Action.
U.S. Appl. No. 14/577,852, Apr. 25, 2018, Notice of Allowance.
U.S. Appl. No. 15/347,543, Dec. 28, 2018, Office Action.
U.S. Appl. No. 15/354,644, Nov. 5, 2018, Office Action.

\* cited by examiner

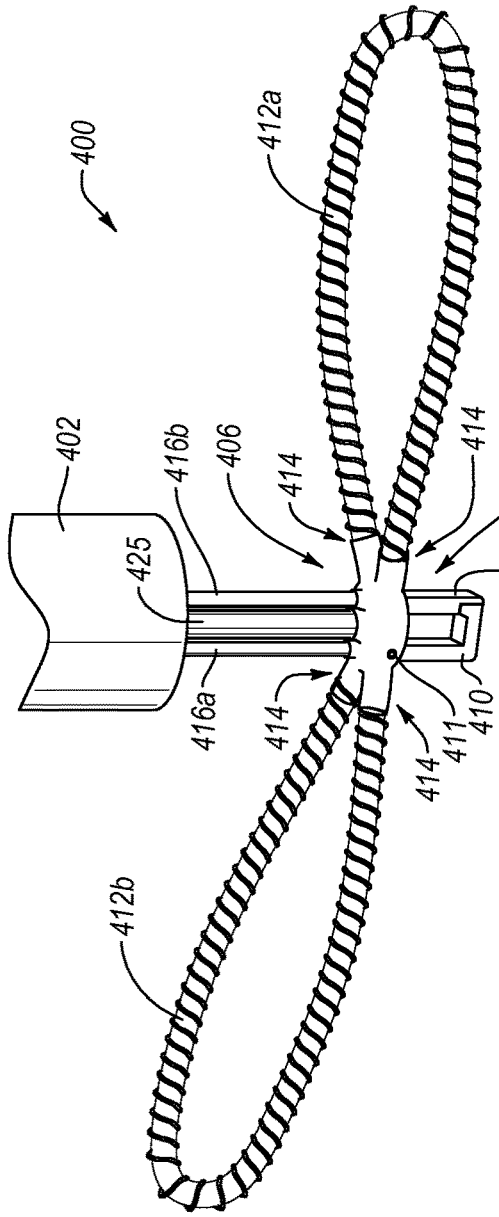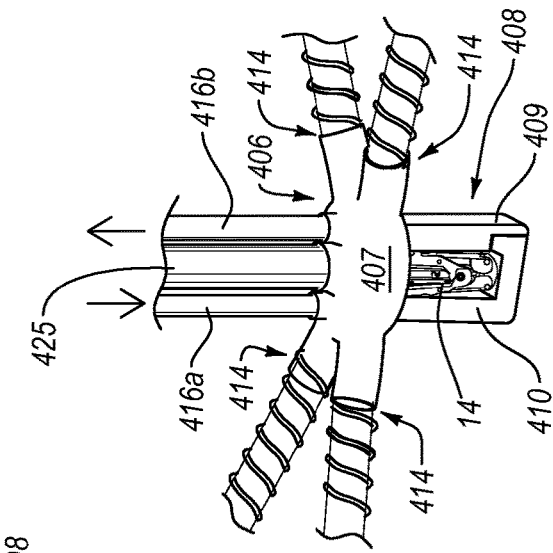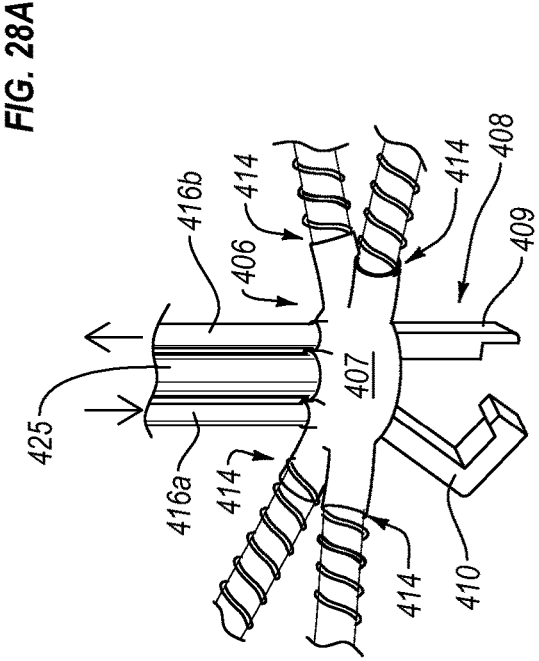
FIG. 28A
FIG. 28B
FIG. 28C

DOUBLE ORIFICE DEVICE FOR TRANSCATHETER MITRAL VALVE REPLACEMENT

BACKGROUND

The present invention relates generally to medical methods, devices, and systems. In particular, the present invention relates to methods, devices, and systems for the endovascular, percutaneous or minimally invasive surgical treatment for replacing a malfunctioning mitral valve within the heart.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles themselves or the left ventricular wall may be damaged or otherwise dysfunctional. Commonly, the valve annulus may be damaged, dilated, or weakened, limiting the ability of the mitral valve to close adequately against the high pressures of the left ventricle.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bow-tie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

In some patients, a fixation device can be installed into the heart using minimally invasive techniques. The fixation device can hold the adjacent segments of the opposed valve leaflets together and may reduce mitral valve regurgitation. One such device used to clip the anterior and posterior leaflets of the mitral valve together is the MitraClip® fixation device, sold by Abbott Vascular, Santa Clara, Calif., USA.

However, sometimes after a fixation device is installed, undesirable mitral valve regurgitation can still exist, or can arise again. As such, it would be desirable to provide devices and methods that would allow for replacement of a malfunctioning mitral valve Such devices and methods should preferably not require open chest access and be capable of being performed endovascularly or other minimally invasive approach, e.g., advancing the device to the heart from a point in the patient's vasculature remote from the heart.

DESCRIPTION OF THE BACKGROUND ART

Minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759; WO 2000/060995; WO 2004/103162. Maisano et al. (1998) Eur. J. Cardiothorac. Surg. 13:240-246; Fucci et al. (1995) Eur. J. Cardiothorac. Surg. 9:621-627; and Umana et al. (1998) Ann. Thorac. Surg. 66:1640-1646, describe open surgical procedures for performing "edge-to-edge" or "bow-tie" mitral valve repair where edges of the opposed valve leaflets are sutured together to lessen regurgitation. Dec and Fuster (1994) N. Engl. J. Med. 331:1564-1575 and Alvarez et al. (1996) J. Thorac. Cardiovasc. Surg. 112:238-247 are review articles discussing the nature of and treatments for dilated cardiomyopathy.

Mitral valve annuloplasty is described in the following publications: Bach and Bolling (1996) Am. J. Cardiol. 78:966-969; Kameda et al. (1996) Ann. Thorac. Surg. 61:1829-1832; Bach and Bolling (1995) Am. Heart J. 129: 1165-1170; and Bolling et al. (1995) 109:676-683. Linear segmental annuloplasty for mitral valve repair is described in Ricchi et al. (1997) Ann. Thorac. Surg. 63:1805-1806. Tricuspid valve annuloplasty is described in McCarthy and Cosgrove (1997) Ann. Thorac. Surg. 64:267-268; Tager et al. (1998) Am. J. Cardiol. 81:1013-1016; and Abe et al. (1989) Ann. Thorac. Surg. 48:670-676.

Percutaneous transluminal cardiac repair procedures are described in Park et al. (1978) Circulation 58:600-608; Uchida et al. (1991) Am. Heart J. 121: 1221-1224; and Ali Khan et al. (1991) Cathet. Cardiovasc. Diagn. 23:257-262. Endovascular cardiac valve replacement is described in U.S. Pat. Nos. 5,840,081; 5,411,552; 5,554,185; 5,332,402; 4,994,077; and 4,056,854. U.S. Pat. No. 3,671,979 describes a catheter for temporary placement of an artificial heart valve.

Other percutaneous and endovascular cardiac repair procedures are described in U.S. Pat. Nos. 4,917,089; 4,484, 579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769, 812; and 5,718,725.

BRIEF SUMMARY

The present disclosure describes methods and devices that may be employed in replacing a mitral valve. For example, according to an embodiment, an orifice valve device for attachment to a mitral valve is provided. The device may include an anchoring and manifold assembly that is coupleable to a delivery catheter. The anchoring and manifold assembly may include means for anchoring the valve device to the mitral valve or to a fixation device that is attached to the mitral valve. The device may further include a peripheral ring anchoring system and a trap door valve, each of which may be secured to the anchoring and manifold assembly. The peripheral ring anchoring system may include at least one expandable anchoring ring that can be expanded within an orifice of the mitral valve so as to surround a perimeter of the orifice of the mitral valve. The ring anchoring system may further include a helical suture that is helically disposeable about the anchoring ring that secures the expandable ring to leaflet tissue around the perimeter of the orifice. The trap door valve may be hingedly secured to the anchoring and manifold assembly, the ring anchoring system, or both, and may include a trap door body that selectively seals against the expandable anchoring ring extending around the perimeter of the orifice of the mitral valve during the systole portion of a cardiac cycle. The trap door body may selectively unseal relative to the expandable anchoring ring so as to open the orifice of the mitral valve during the diastole portion of the cardiac cycle.

Another embodiment is directed to a double orifice valve device for attachment to the mitral valve. The device may include an anchoring and manifold assembly that is coupleable to a delivery catheter. The anchoring and manifold assembly may include means for anchoring the valve device to the mitral valve or to a fixation device that is attached to the mitral valve. The device may further include a peripheral ring anchoring system and a pair of trap door valves, each of which may be secured to the anchoring and manifold assembly. The peripheral ring anchoring system may include a pair of expandable anchoring rings that can be expanded within respective orifices of the mitral valve so as to surround a perimeter of the respective orifice of the mitral valve. The ring anchoring system may further include a helical suture that is helically disposeable about each of the anchoring rings so as to secure each expandable ring to leaflet tissue around the perimeter of each respective orifice. Each trap door valve may be hingedly secured to the anchoring and manifold assembly, the ring anchoring system, or both, and may each include a trap door body that selectively seals against the respective expandable anchoring ring extending around the perimeter of the respective orifice of the mitral valve during the systole portion of a cardiac cycle. Each trap door body may selectively unseal relative to the respective expandable anchoring ring so as to open the respective orifice of the mitral valve during the diastole portion of the cardiac cycle. For example, the two anchoring rings and associated trap door valves may be disposed on opposed sides of the anchoring and manifold assembly, so that one anchoring ring and trap door valve is associated with one of the respective orifices of a mitral valve where opposed leaflets (e.g., A2 and P2 segments) of the mitral valve have been coapted together with a fixation device.

Another embodiment of the present disclosure is directed to a method for replacing a malfunctioning mitral valve (e.g., exhibiting an undesirable degree of regurgitation) with a mitral orifice valve. Such a method may be achieved using minimally invasive techniques (e.g., endovascularly). The method may include delivering a mitral orifice valve device into the heart of a patient (e.g., delivery through a minimally invasive endovascular procedure using a delivery catheter positioned in the heart), and anchoring the mitral orifice valve device to the mitral valve or a fixation device that is attached to the mitral valve. An expandable anchoring ring of the device may be expanded within an orifice of the mitral valve so that the expandable anchoring ring surrounds a perimeter of the orifice of the mitral valve. The anchoring ring may be secured to leaflet tissue around the perimeter of the orifice (e.g., by suturing). A trap door valve of the valve device may be deployed, which trap door valve selectively seals against the anchoring ring extending around the perimeter of the orifice, so that during the systole portion of the cardiac cycle the orifice is closed, and during the diastole portion of the cardiac cycle the orifice is opened.

Any of such described methods and devices may advantageously be employed with minimal invasion, e.g., through an endovascular procedure that advances the valve device through the vasculature of the patient, into the heart, where the device may be deployed adjacent the mitral valve, for attachment thereto.

These and other objects and features of the present disclosure will become more fully apparent from the following description and appended claims, or may be learned by the practice of the embodiments of the invention as set forth hereinafter.

BRIEF DESCRIPTION OF THE DRAWINGS

To further clarify the above and other advantages and features of the present disclosure, a more particular description of the invention will be rendered by reference to specific embodiments thereof which are illustrated in the appended drawings. It is appreciated that these drawings depict only illustrated embodiments of the invention and are therefore not to be considered limiting of its scope. Embodiments of the invention will be described and explained with additional specificity and detail through the use of the accompanying drawings in which:

FIG. 28A illustrates the valve device of FIG. 27 once it has been deployed from the delivery catheter, so that the flexible expandable anchoring rings have been released from the delivery catheter.

FIG. 28B illustrates the valve device of FIG. 28A with the movable arm of a basket for capturing at least a portion of a fixation device in an opened position, so as to capture the fixation device within the basket and anchor the valve device to the fixation device.

FIG. 28C illustrates the valve device of FIG. 28B with the movable arm closed around the fixation device so as to anchor the valve device to the fixation device.

FIG. 32A shows an elevational view with the trap door body of the trap door valve in a closed and open position (shown in phantom).

DETAILED DESCRIPTION

I. Introduction

A. Cardiac Physiology

Figure 1:
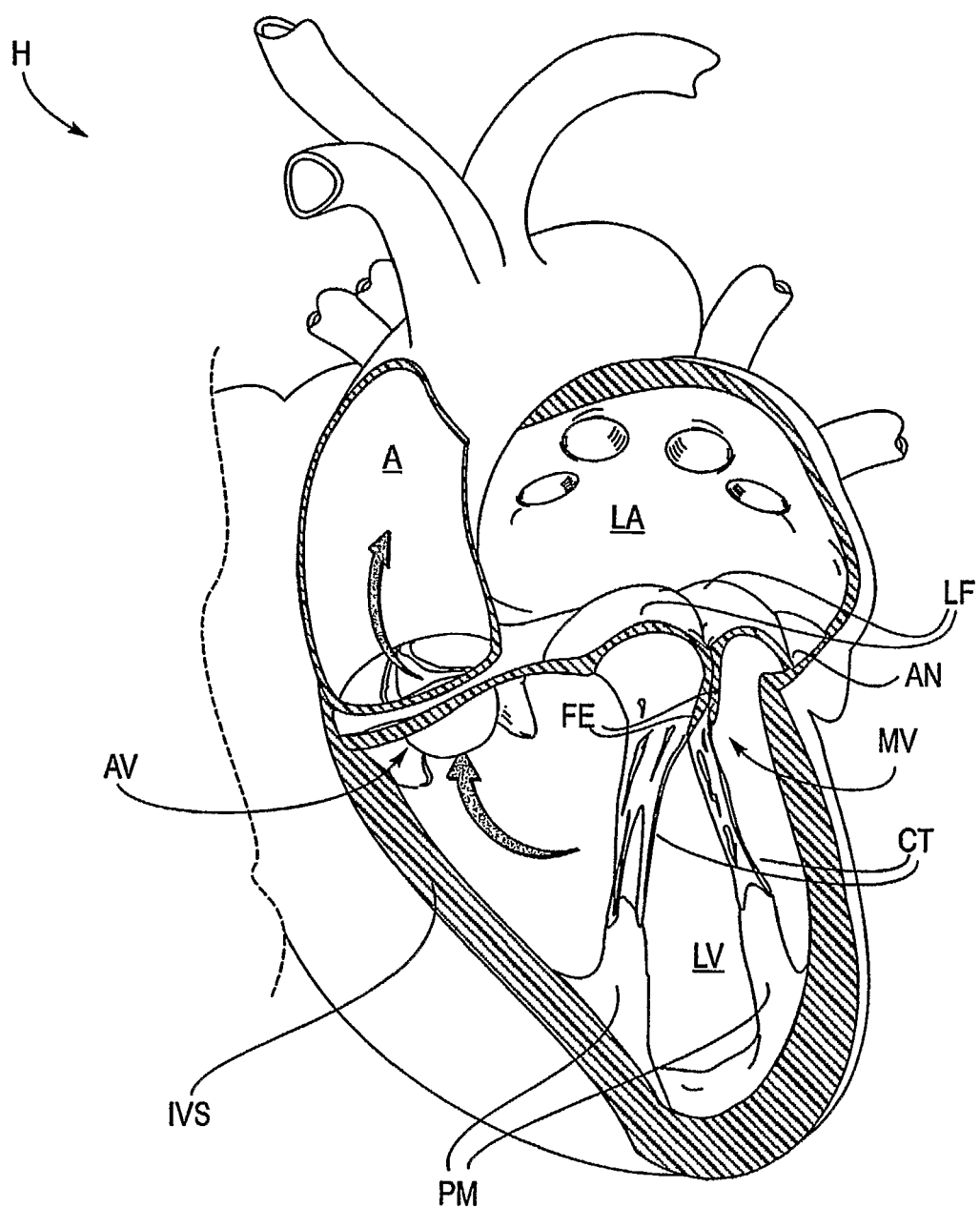
FIG. 1 illustrates the left ventricle and left atrium of the heart during systole.

The left ventricle LV of a normal heart H in systole is illustrated in FIG. 1. The left ventricle LV is contracting and blood flows outwardly through the tricuspid (aortic) valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendinae CT (referred to hereinafter as the chordae) which include a plurality of branching tendons secured over the lower surfaces of each of the valve leaflets LF. The chordae CT in turn, are attached to the papillary muscles PM which extend upwardly from the lower portions of the left ventricle and intraventricular septum IVS.

Figure 2A:
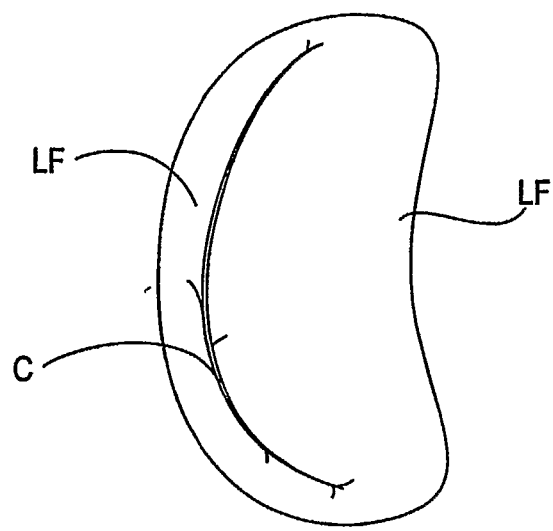
FIG. 2A illustrates free edges of leaflets of the mitral valve in normal coaptation.
Figure 2B:
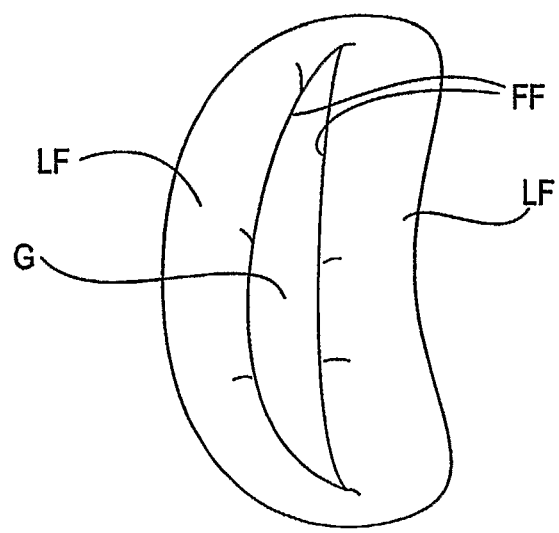
FIG. 2B illustrates the free edges in regurgitative coaptation.

A number of structural defects in the heart can cause mitral valve regurgitation. Regurgitation occurs when the valve leaflets do not close properly allowing leakage from the ventricle into the atrium. As shown in FIG. 2A, the free edges of the anterior and posterior leaflets normally meet along a line of coaptation (C). An example of a defect causing regurgitation is shown in FIG. 2B. Here an enlargement of the heart causes the mitral annulus to become enlarged, making it impossible for the free edges (FE) to meet during systole. This results in a gap (G) which allows blood to leak through the valve during ventricular systole. Ruptured or elongated chordae can also cause a valve leaflet to prolapse since inadequate tension is transmitted to the leaflet via the chordae. While the other leaflet maintains a normal profile, the two valve leaflets do not properly meet and leakage from the left ventricle into the left atrium will occur. Such regurgitation can also occur in patients who have suffered ischemic heart disease where the left ventricle does not contract sufficiently to effect proper closure.

II. General Overview of Mitral Valve Fixation Technology

In an embodiment, the valve devices of the present invention may be anchored to a fixation device such as those currently employed in fixation of the mitral valve to treat mitral valve regurgitation. In another embodiment, the valve device may incorporate a grasping mechanism similar to that of such a fixation device, where the valve device is to be installed in a mitral valve that does not include a fixation device (or where the fixation device has been removed or disabled). An example of such a fixation device is the MitraClip® fixation device, referenced above. As such, a description of such fixation devices and methods for their placement will now be provided.

Fixation devices are used for grasping, approximating and fixating tissues such as valve leaflets to treat cardiac valve regurgitation, particularly mitral valve regurgitation. The fixation devices may also provide features that allow repositioning and removal of the device if so desired, particularly in areas where removal may be hindered by anatomical features such as chordae CT. Such removal would allow the surgeon to reapproach the valve in a new manner if so desired.

Grasping will preferably be atraumatic providing a number of benefits. By atraumatic, it is meant that the fixation device may be applied to the valve leaflets and then removed without causing any significant clinical impairment of leaflet structure or function. The leaflets and valve continue to function substantially the same as before the fixation devices are applied. Thus, some minor penetration or denting of the leaflets may occur using the devices while still meeting the definition of "atraumatic." Similarly, during disabling or removal of the fixation device, a small portion of the leaflet(s) may be cut around the edges of the fixation device. Such atraumatic installation, disabling, or removal enables the devices to be applied to a diseased valve and, if desired, removed or repositioned without having negatively affected valve function. In addition, it will be understood that in some cases it may be necessary or desirable to pierce or otherwise permanently affect the leaflets during either grasping, fixing and/or removal. Grasping and fixation may be accomplished by a single or multiple devices.

The fixation devices may rely upon the use of an interventional tool that is positioned near a desired treatment site and used to grasp the target tissue. In endovascular applications, the interventional tool is typically an interventional catheter. In surgical applications, the interventional tool is typically an interventional instrument. Fixation of the grasped tissue is accomplished by maintaining grasping with a portion of the interventional tool which is left behind as an implant.

Figure 3A:
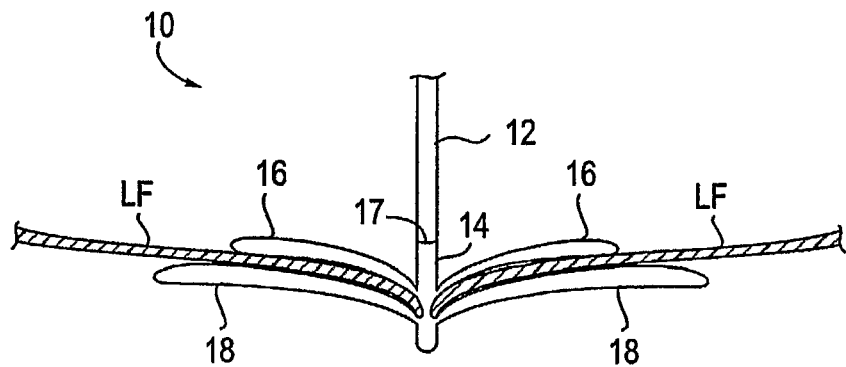
FIGS. 3A-3C illustrate grasping of the leaflets with a fixation device, inversion of the distal elements of the fixation device and removal of the fixation device, respectively.

Referring to FIG. 3A, an interventional tool 10, having a delivery device, such as a shaft 12, and a fixation device 14, is illustrated having approached the mitral valve MV from the atrial side and grasped the leaflets LF. The mitral valve may be accessed either surgically or by using endovascular techniques, and either by a retrograde approach through the ventricle or by an antegrade approach through the atrium. For illustration purposes, an antegrade approach is described.

The fixation device 14 is releasably attached to the shaft 12 of the interventional tool 10 at its distal end. When describing the devices of the invention herein, "proximal" shall mean the direction toward the end of the device to be manipulated by the user outside the patient's body, and "distal" shall mean the direction toward the working end of the device that is positioned at the treatment site and away from the user. With respect to the mitral valve, proximal shall refer to the atrial or upstream side of the valve leaflets and distal shall refer to the ventricular or downstream side of the valve leaflets.

The fixation device 14 typically comprises proximal elements 16 (or gripping elements) and distal elements 18 (or fixation elements) which protrude radially outward and are positionable on opposite sides of the leaflets LF as shown so as to capture or retain the leaflets therebetween. The proximal elements 16 are preferably comprised of cobalt chromium, nitinol or stainless steel, and the distal elements 18 are preferably comprised of cobalt chromium, stainless steel, or other material. The fixation device 14 is coupleable to the shaft 12 by a coupling mechanism 17. The coupling mechanism 17 allows the fixation device 14 to detach and be left behind as an implant to hold the leaflets together in the coapted position.

In some situations, it may be desired to reposition or remove the fixation device 14 after the proximal elements 16, distal elements 18, or both have been deployed to capture the leaflets LF. Such repositioning or removal may be desired for a variety of reasons, such as to reapproach the valve in an attempt to achieve better valve function, more optimal positioning of the device 14 on the leaflets, better purchase on the leaflets, to detangle the device 14 from surrounding tissue such as chordae, to exchange the device 14 with one having a different design, or to abort the fixation procedure, to name a few. To facilitate repositioning or removal of the fixation device 14 the distal elements 18 may be released and optionally inverted to a configuration suitable for withdrawal of the device 14 from the valve without tangling or interfering with or damaging the chordae, leaflets or other tissue.

Figure 3B:
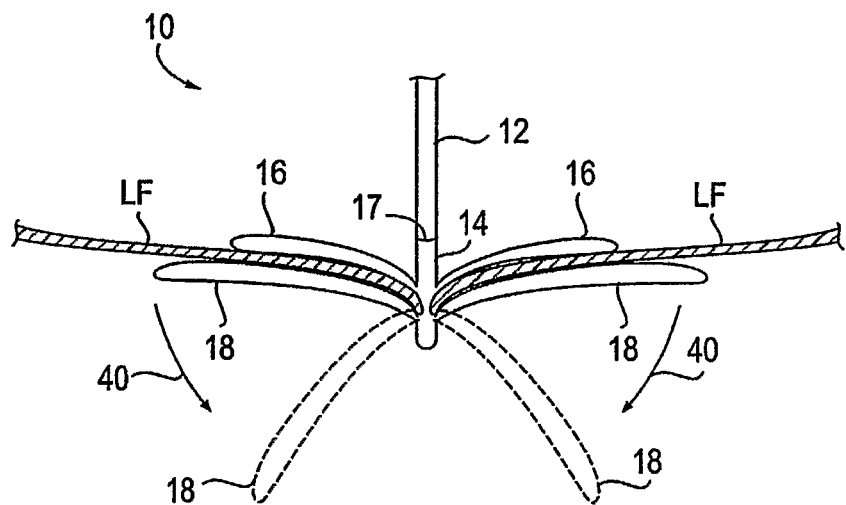
Figure 3C:
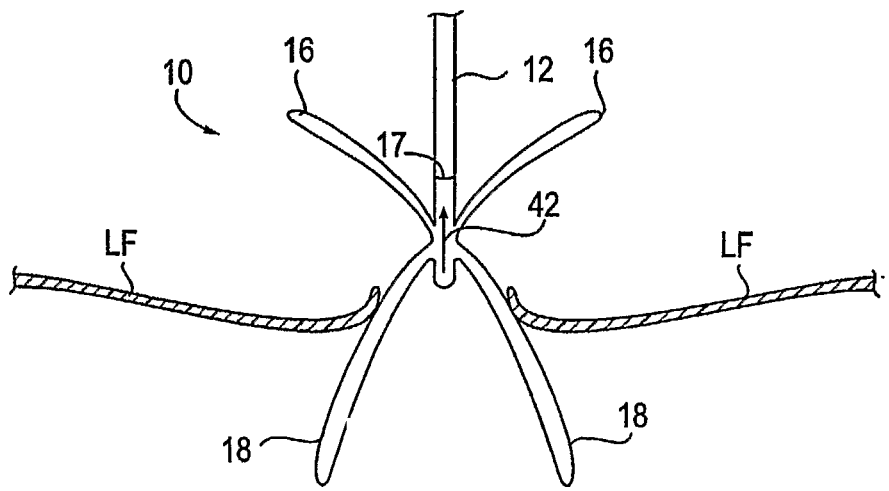

FIG. 3B illustrates inversion wherein the distal elements 18 are moveable in the direction of arrows 40 to an inverted position. Likewise, the proximal elements 16 may be raised, if desired. In the inverted position, the device 14 may be repositioned to a desired orientation wherein the distal elements may then be reverted to a grasping position against the leaflets as in FIG. 3A. Alternatively, the fixation device 14 may be withdrawn (indicated by arrow 42) from the leaflets as shown in FIG. 3C. Such inversion reduces trauma to the leaflets and minimizes any entanglement of the device with surrounding tissues. Once the device 14 has been withdrawn through the valve leaflets, the proximal and distal elements may be moved to a closed position or configuration suitable for removal from the body or for reinsertion through the mitral valve.

Figure 4:
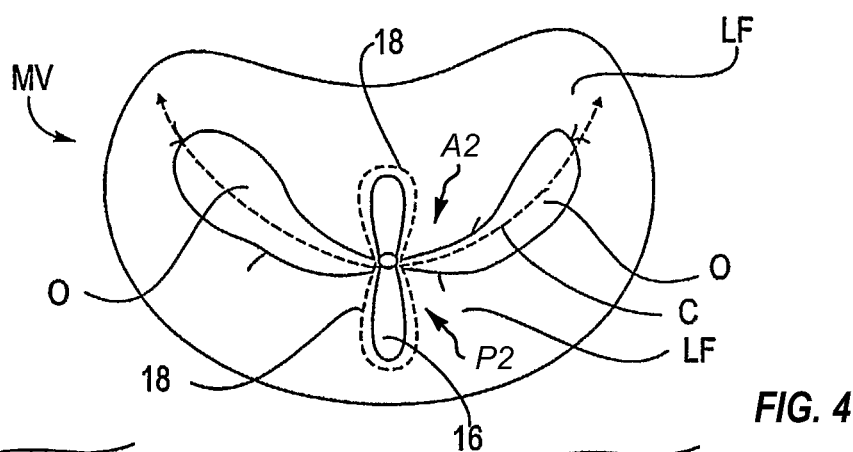
FIG. 4 illustrates the position of the fixation device in a typical orientation relative to the leaflets.

FIG. 4 illustrates the position of the fixation device 14 in a desired orientation in relation to the leaflets LF. This is a short-axis view of the mitral valve MV from the atrial side, therefore, the proximal elements 16 are shown in solid line and the distal elements 18 are shown in dashed line. The proximal and distal elements 16, 18 are positioned to be substantially perpendicular to the line of coaptation C. The device 14 may be moved roughly along the line of coaptation to the location of regurgitation. The leaflets LF are held in place so that during diastole, as shown in FIG. 4, the leaflets LF remain in position between the elements 16, 18 surrounded by openings or orifices O which result from the diastolic pressure gradient. Advantageously, leaflets LF are coapted such that their proximal or upstream surfaces are facing each other in a vertical orientation, parallel to the direction of blood flow through mitral valve MV. The upstream surfaces may be brought together so as to be in contact with one another or may be held slightly apart, but will preferably be maintained in the vertical orientation in which the upstream surfaces face each other at the point of coaptation. This simulates the double orifice geometry of a standard surgical bow-tie repair. Color Doppler echo will show if the regurgitation of the valve has been reduced. If the resulting mitral flow pattern is satisfactory, the leaflets may be fixed together in this orientation. If the resulting color Doppler image shows insufficient improvement in mitral regurgitation, the interventional tool 10 may be repositioned. This may be repeated until an optimal result is produced wherein the leaflets LF are held in place.

Figure 5A:
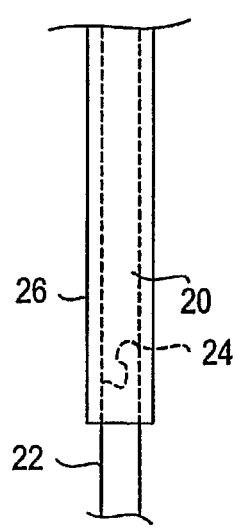
FIGS. 5A-5B, 6A-6B illustrate exemplary coupling mechanisms for coupling a fixation device to a shaft of a delivery catheter.
Figure 5B:
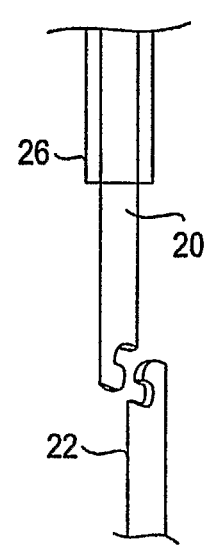

Once the leaflets are coapted in the desired arrangement, the fixation device 14 is then detached from the shaft 12 and left behind as an implant to hold the leaflets together in the coapted position. As mentioned previously, the fixation device 14 is coupled to the shaft 12 by a coupling mechanism 17. FIGS. 5A-5B, 6A-6B illustrate examples of such coupling mechanisms. FIG. 5A shows an upper shaft 20 and a detachable lower shaft 22 which are interlocked at a joining line or mating surface 24. The mating surface 24 may have any shape or curvature which will allow or facilitate interlocking and later detachment. A snuggly fitting outer sheath 26 is positioned over the shafts 20, 22 to cover the mating surface 24 as shown. FIG. 5B illustrates detachment of the lower shaft 22 from the upper shaft 20. This is achieved by retracting the outer sheath 26, so that the mating surface 24 is exposed, which allows the shafts 20, 22 to separate.

Figure 6A:
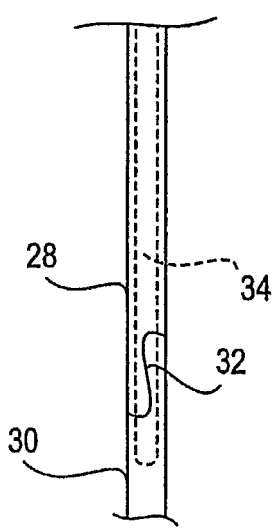
Figure 6B:
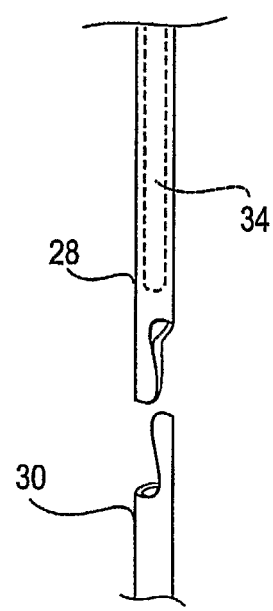

Similarly, FIG. 6A illustrates a tubular upper shaft 28 and a detachable tubular lower shaft 30 which are interlocked at a mating surface 32. Again, the mating surface 32 may have any shape or curvature which will allow or facilitate interlocking and later detachment. The tubular upper shaft 28 and tubular lower shaft 30 form an outer member having an axial channel. A snuggly fitting rod 34 or inner member is inserted through the tubular shafts 28, 30 to bridge the mating surface 32 as shown. FIG. 6B illustrates detachment of the lower shaft 30 from the upper shaft 28. This is achieved by retracting the rod 34 to a position above the mating surface 32 which in turn allows the shafts 28, 30 to separate.

The mating surface 24 (or mating surface 32) is a sigmoid curve defining a male element and female element on upper shaft 20 (or upper shaft 28) which interlock respectively with corresponding female and male elements on lower shaft 22 (or lower shaft 30). Typically, the lower shaft is the coupling mechanism 17 of the fixation device 14. Therefore, the shape of the mating surface selected will preferably provide at least some mating surfaces transverse to the axial axis of the mechanism 19 to facilitate application of compressive and tensile forces through the coupling mechanism 17 to the fixation device 14, yet causing minimal interference when the fixation device 14 is to be released from the upper shaft.

It will be apparent that other coupling mechanisms may alternatively be employed.

A. Exemplary Fixation Device

Figure 7:
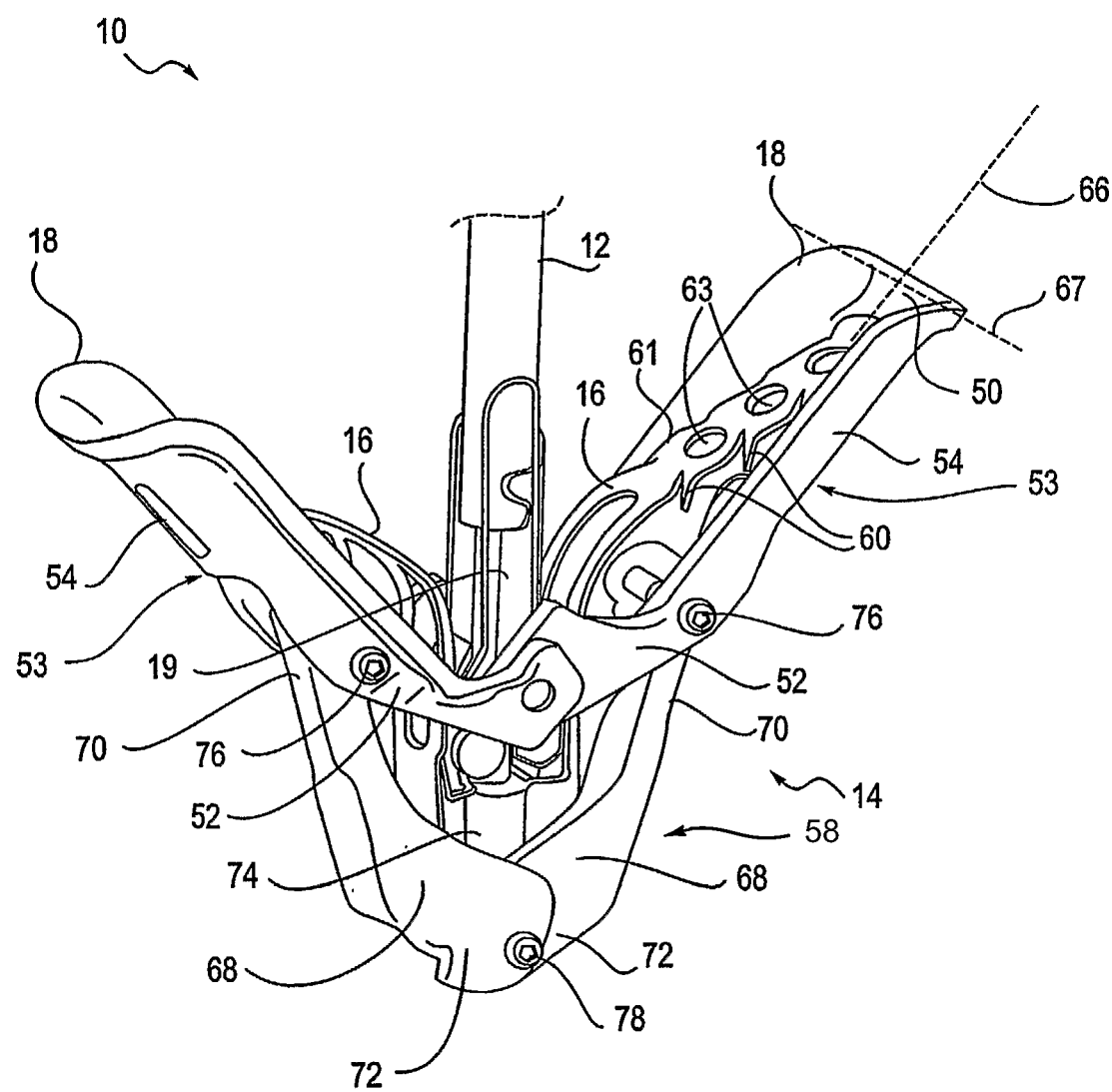
FIG. 7 illustrates an exemplary fixation device coupled to a shaft.

FIG. 7 illustrates an exemplary fixation device 14. The valve devices of the present invention may be anchored to such a fixation device, or may incorporate a grasping mechanism for engaging the mitral valve leaflet tissue similar to fixation device 14. Here, the fixation device 14 is shown coupled to a shaft 12 to form an interventional tool 10. The fixation device 14 includes a coupling member 19 and a pair of opposed distal elements 18. The distal elements 18 comprise elongate arms 53, each arm having a proximal end 52 rotatably connected to the coupling member 19 and a free end 54. The free ends 54 have a rounded shape to minimize interference with and trauma to surrounding tissue structures. Preferably, each free end 54 defines a curvature about two axes, one being an axis 66 perpendicular to longitudinal axis of arms 53. Thus, the engagement surfaces 50 have a cupped or concave shape to the surface area in contact with tissue and to assist in grasping and holding the valve leaflets. This further allows arms 53 to nest around the shaft 12 in the closed position to minimize the profile of the device. Preferably, arms 53 are at least partially cupped or curved inwardly about their longitudinal axes 66. Also, preferably, each free end 54 defines a curvature about an axis 67 perpendicular to axis 66 or the longitudinal axis of arms 53. This curvature is a reverse curvature along the most distal portion of the free end 54. Likewise, the longitudinal edges of the free ends 54 may flare outwardly. Both the reverse curvature and flaring minimize trauma to the tissue engaged therewith.

To be suitable for mitral valve repair, the transverse width across engagement surfaces 50 (which determines the width of tissue engaged) may be at least about 2 mm, usually 3-10 mm, and preferably about 4-6 mm. In some situations, a wider engagement is desired wherein the engagement surfaces 50 are larger, for example about 2 cm, or multiple fixation devices are used adjacent to each other. Arms 53 and engagement surfaces 50 are configured to engage a length of tissue of about 4-10 mm, and preferably about 6-8 mm along the longitudinal axis of arms 53. Arms 53 further include a plurality of openings to enhance grip and to promote tissue ingrowth following implantation.

The valve leaflets are grasped between the distal elements 18 and proximal elements 16. The proximal elements 16 may be flexible, resilient, and cantilevered from coupling member 19. The proximal elements are preferably resiliently biased toward the distal elements. Each proximal element 16 is shaped and positioned to be at least partially recessed within the concavity of the distal element 18 when no tissue is present. When the fixation device 14 is in the open position, the proximal elements 16 are shaped such that each proximal element 16 is separated from the engagement surface 50 near the proximal end 52 of arm 53 and slopes toward the engagement surface 50 near the free end 54 with the free end of the proximal element contacting engagement surface 50, as illustrated in FIG. 7. This shape of the proximal elements 16 accommodates valve leaflets or other tissues of varying thicknesses.

Proximal elements 16 include a plurality of openings 63 and scalloped side edges 61 to increase grip on tissue. The proximal elements 16 optionally include frictional accessories, frictional features or grip-enhancing elements to assist in grasping and/or holding the leaflets. The frictional accessories may comprise barbs 60 having tapering pointed tips extending toward engagement surfaces 50. Any suitable frictional accessories may be used, such as prongs, windings, bands, barbs, grooves, channels, bumps, surface roughening, sintering, high-friction pads, coverings, coatings or a combination of these. Optionally, magnets may be present in the proximal and/or distal elements. It may be appreciated that the mating surfaces will be made from or will include material of opposite magnetic charge to cause attraction by magnetic force. For example, the proximal elements and distal elements may each include magnetic material of opposite charge so that tissue is held under constant compression between the proximal and distal elements to facilitate faster healing and ingrowth of tissue. Also, the magnetic force may be used to draw the proximal elements 16 toward the distal elements 18, in addition to or alternatively to biasing of the proximal elements toward the distal elements. This may assist in deployment of the proximal elements 16. In another example, the distal elements 18 each include magnetic material of opposite charge so that tissue positioned between the distal elements 18 is held therebetween by magnetic force.

The proximal elements 16 may be covered with a fabric or other flexible material as described below to enhance grip and tissue ingrowth following implantation. Preferably, when fabrics or coverings are used in combination with barbs or other frictional features, such features will protrude through such fabric or other covering so as to contact any tissue engaged by proximal elements 16.

Proximal elements 16 may be formed from metallic sheet of a spring-like material using a stamping operation which creates openings 63, scalloped edges 61 and barbs 60. Alternatively, proximal elements 16 could be comprised of a spring-like material or molded from a biocompatible polymer. Some types of frictional accessories may permanently alter or cause some trauma to the tissue engaged thereby, whereas other frictional accessories will be atraumatic and will not injure or otherwise affect the tissue in a clinically significant way. For example, in the case of barbs 60, it has been demonstrated that following engagement of mitral valve leaflets by fixation device 14, should the device later be removed during the procedure barbs 60 leave no significant permanent scarring or other impairment of the leaflet tissue and are thus considered atraumatic.

The fixation device 14 also includes an actuation mechanism 58. The actuation mechanism 58 comprises two link members or legs 68, each leg 68 having a first end 70 which is rotatably joined with one of the distal elements 18 at a riveted joint 76 and a second end 72 which is rotatably joined with a stud 74. The legs 68 are preferably comprised of a rigid or semi-rigid metal or polymer such as Elgiloy®, cobalt chromium, stainless steel, or other material. While in the device illustrated both legs 68 are pinned to stud 74 by a single rivet 78, it may be appreciated, however, that each leg 68 may be individually attached to the stud 74 by a separate rivet or pin. The stud 74 is joinable with an actuator rod 64 (not shown) which extends through the shaft 12 and is axially extendable and retractable to move the stud 74 and therefore the legs 68 which rotate the distal elements 18 between closed, open and inverted positions. Likewise, immobilization of the stud 74 holds the legs 68 in place and therefore holds the distal elements 18 in a desired position. The stud 74 may also be locked in place by a locking feature which will be further described in later sections.

There may be some mobility or flexibility in distal elements 18 and/or proximal elements 16 of the fixation device 14 in the closed position to enable these elements to move or flex with the opening or closing of the valve leaflets. This provides shock absorption and thereby reduces force on the leaflets and minimizes the possibility for tearing or other trauma to the leaflets. Such mobility or flexibility may be provided by using a flexible, resilient metal or polymer of appropriate thickness to construct the distal elements 18. Also, the locking mechanism of the fixation device (described below) may be constructed of flexible materials to allow some slight movement of the proximal and distal elements even when locked. Further, the distal elements 18 can be connected to the coupling mechanism 19 or to actuation mechanism 58 by a mechanism that biases the distal element into the closed position (inwardly) but permits the arms to open slightly in response to forces exerted by the leaflets. For example, rather than being pinned at a single point, these components may be pinned through a slot that allows a small amount of translation of the pin in response to forces against the arms. A spring may be used to bias the pinned component toward one end of the slot.

Figure 8A:
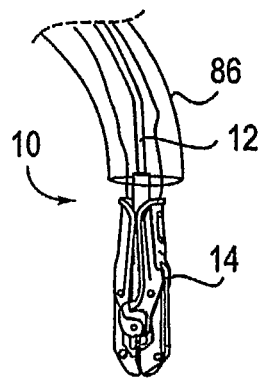
FIGS. 8A-8B, 9A-9B, 10A-10B, 11A-11B, and FIGS. 12-14 illustrate a fixation device in various possible positions during introduction and placement of the device within the body to perform a therapeutic procedure.
Figure 8B:
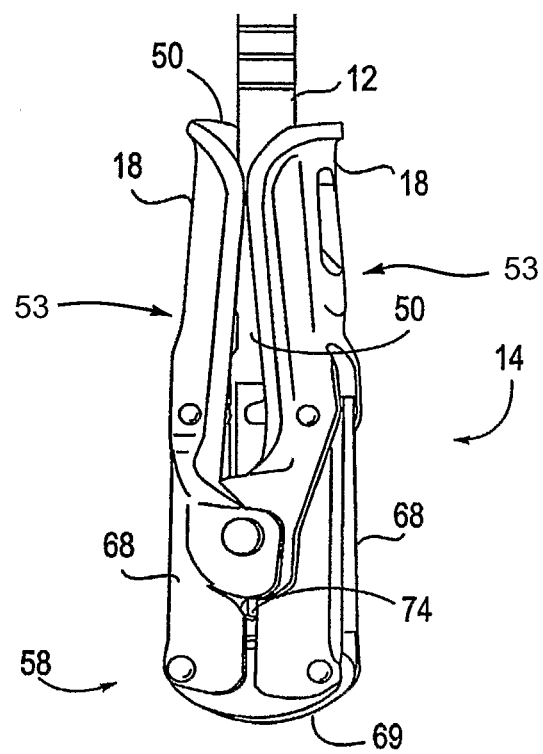

FIGS. 8A-8B, 9A-9B, 10A-10B, 11A-11B, and FIGS. 12-14 illustrate various possible positions of the fixation device 14 of FIG. 7 during introduction and placement of the device 14 within the body to perform a therapeutic procedure. FIG. 8A illustrates an interventional tool 10 delivered through a catheter 86. It may be appreciated that the interventional tool 10 may take the form of a catheter, and likewise, the catheter 86 may take the form of a guide catheter or sheath. However, in this example the terms interventional tool 10 and catheter 86 will be used. The interventional tool 10 comprises a fixation device 14 coupled to a shaft 12 and the fixation device 14 is shown in the closed position. FIG. 8B illustrates a device similar to the device of FIG. 8A in a larger view. In the closed position, the opposed pair of distal elements 18 are positioned so that the engagement surfaces 50 face each other. Each distal element 18 comprises an elongate arm 53 having a cupped or concave shape so that together the aims 53 surround the shaft 12 and optionally contact each other on opposite sides of the shaft. This provides a low profile for the fixation device 14 which is readily passable through the catheter 86 and through any anatomical structures, such as the mitral valve. In addition, FIG. 8B further includes an actuation mechanism 58. The actuation mechanism 58 comprises two legs 68 which are each movably coupled to a base 69. The base 69 is joined with an actuator rod 64 which extends through the shaft 12 and is used to manipulate the fixation device 14. The actuator rod 64 may attach directly to the actuation mechanism 58, particularly the base 69. However, the actuator rod 64 may alternatively attach to a stud 74 which in turn is attached to the base 69. The stud 74 may be threaded so that the actuator rod 64 attaches to the stud 74 by a screw-type action. However, the rod 64 and stud 74 may be joined by any mechanism which is releasable to allow the fixation device 14 to be detached from shaft 12.

Figure 9A:
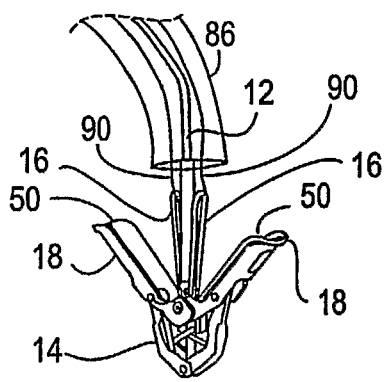
Figure 9B:
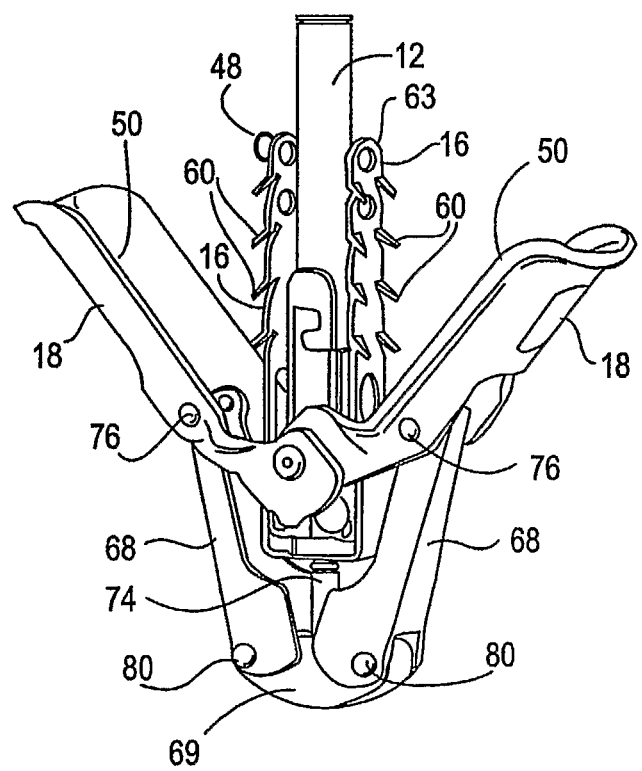

FIGS. 9A-9B illustrate the fixation device 14 in the open position. In the open position, the distal elements 18 are rotated so that the engagement surfaces 50 face a first direction. Distal advancement of the stud 74 relative to coupling member 19 by action of the actuator rod 64 applies force to the distal elements 18 which begin to rotate around joints 76 due to freedom of movement in this direction. Such rotation and movement of the distal elements 18 radially outward causes rotation of the legs 68 about joints 80 so that the legs 68 are directed slightly outwards. The stud 74 may be advanced to any desired distance correlating to a desired separation of the distal elements 18. In the open position, engagement surfaces 50 are disposed at an acute angle relative to shaft 12, and are preferably at an angle of between 90 and 180 degrees relative to each other. In the open position, the free ends 54 of arms 53 may have a span therebetween of about 10-20 mm, usually about 12-18 mm, and preferably about 14-16 mm.

Proximal elements 16 are typically biased outwardly toward arms 53. The proximal elements 16 may be moved inwardly toward the shaft 12 and held against the shaft 12 with the aid of proximal element lines 90 which can be in the form of sutures, wires, nitinol wire, rods, cables, polymeric lines, or other suitable structures. The proximal element lines 90 may be connected with the proximal elements 16 by threading the lines 90 in a variety of ways. When the proximal elements 16 have a loop shape, as shown in FIG. 9A, the line 90 may pass through the loop and double back. When the proximal elements 16 have an elongate solid shape, as shown in FIG. 9B, the line 90 may pass through one or more of the openings 63 in the element 16. Further, a line loop 48 may be present on a proximal element 16, also illustrated in FIG. 9B, through which a proximal element line 90 may pass and double back. Such a line loop 48 may be useful to reduce friction on proximal element line 90 or when the proximal elements 16 are solid or devoid of other loops or openings through which the proximal element lines 90 may attach. A proximal element line 90 may attach to the proximal elements 16 by detachable means which would allow a single line 90 to be attached to a proximal element 16 without doubling back and would allow the single line 90 to be detached directly from the proximal element 16 when desired. Examples of such detachable means include hooks, snares, clips or breakable couplings, to name a few.

By applying sufficient tension to the proximal element line 90, the detachable means may be detached from the proximal element 16 such as by breakage of the coupling. Other mechanisms for detachment may also be used. Similarly, a lock line 92 (FIG. 16) may be attached and detached from a locking mechanism by similar detachable means.

In the open position, the fixation device 14 can engage the tissue which is to be approximated or treated. The device illustrated in FIGS. 7-9B is adapted for repair of the mitral valve using an antegrade approach from the left atrium. The interventional tool 10 is advanced through the mitral valve from the left atrium to the left ventricle. The distal elements 18 are oriented to be perpendicular to the line of coaptation and then positioned so that the engagement surfaces 50 contact the ventricular surface of the valve leaflets, thereby grasping the leaflets. The proximal elements 16 remain on the atrial side of the valve leaflets so that the leaflets lie between the proximal and distal elements. The proximal elements 16 have frictional accessories, such as barbs 60 which are directed toward the distal elements 18. However, neither the proximal elements 16 nor the barbs 60 contact the leaflets at this time.

The interventional tool 10 may be repeatedly manipulated to reposition the fixation device 14 so that the leaflets are properly contacted or grasped at a desired location. Repositioning is achieved with the fixation device in the open position. In some instances, regurgitation may also be checked while the device 14 is in the open position. If regurgitation is not satisfactorily reduced, the device may be repositioned and regurgitation checked again until the desired results are achieved.

Figure 10A:
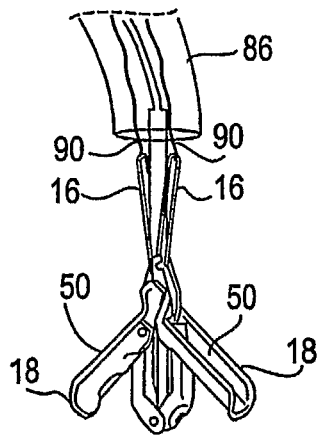
Figure 10B:
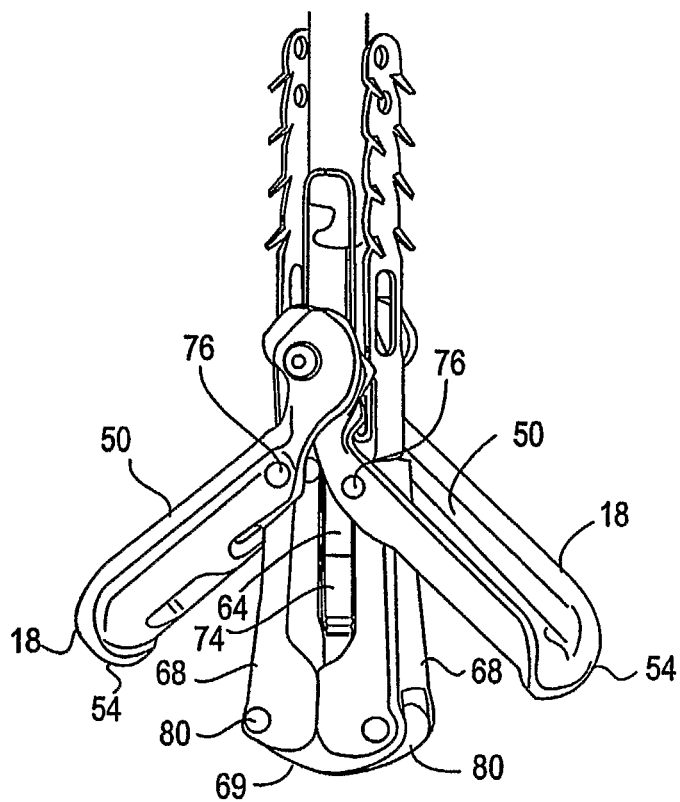

It may also be desired to invert the fixation device 14 to aid in repositioning or removal of the fixation device 14. FIGS. 10A-10B illustrate the fixation device 14 in the inverted position. By further advancement of stud 74 relative to coupling member 19, the distal elements 18 are further rotated so that the engagement surfaces 50 face outwardly and free ends 54 point distally, with each arm 53 forming an obtuse angle relative to shaft 12.

The angle between arms 53 is preferably in the range of about 270 to 360 degrees. Further advancement of the stud 74 further rotates the distal elements 18 around joints 76. This rotation and movement of the distal elements 18 radially outward causes rotation of the legs 68 about joints 80 so that the legs 68 are returned toward their initial position, generally parallel to each other. The stud 74 may be advanced to any desired distance correlating to a desired inversion of the distal elements 18. Preferably, in the fully inverted position, the span between free ends 54 is no more than about 20 mm, usually less than about 16 mm, and preferably about 12-14 mm. In this illustration, the proximal elements 16 remain positioned against the shaft 12 by exerting tension on the proximal element lines 90. Thus, a relatively large space may be created between the elements 16, 18 for repositioning. In addition, the inverted position allows withdrawal of the fixation device 14 through the valve while minimizing trauma to the leaflets. Engagement surfaces 50 provide an atraumatic surface for deflecting tissue as the fixation device is retracted proximally. Barbs 60 are angled slightly in the distal direction (away from the free ends of the proximal elements 16), reducing the risk that the barbs will catch on or lacerate tissue as the fixation device is withdrawn.

Figure 11A:
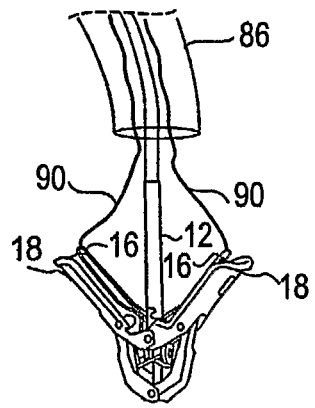
Figure 11B:
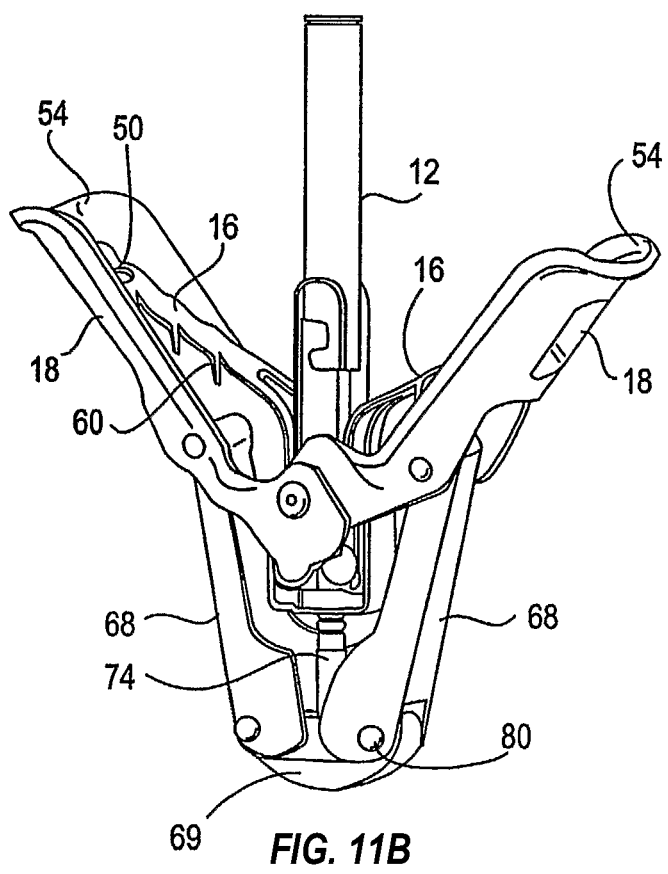

Once the fixation device 14 has been positioned in a desired location against the valve leaflets, the leaflets may then be captured between the proximal elements 16 and the distal elements 18. FIGS. 11A-11B illustrate the fixation device 14 in such a position. Here, the proximal elements 16 are lowered toward the engagement surfaces 50 so that the leaflets are held therebetween. In FIG. 11B, the proximal elements 16 are shown to include barbs 60 which may be used to provide atraumatic gripping of the leaflets. Alternatively, larger, more sharply pointed barbs or other penetration structures may be used to pierce the leaflets to more actively assist in holding them in place. This position is similar to the open position of FIGS. 9A-9B, however the proximal elements 16 are now lowered toward arms 53 by releasing tension on proximal element lines 90 to compress the leaflet tissue therebetween. At any time, the proximal elements 16 may be raised and the distal elements 18 adjusted or inverted to reposition the fixation device 14, if regurgitation is not sufficiently reduced.

Figure 12:
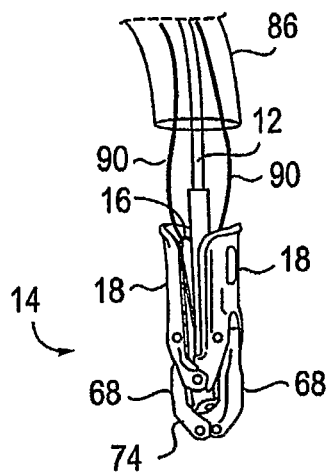

After the leaflets have been captured between the proximal and distal elements 16, 18 in a desired arrangement, the distal elements 18 may be locked to hold the leaflets in this position or the fixation device 14 may be returned to or toward a closed position. Such locking will be described in a later section. FIG. 12 illustrates the fixation device 14 in the closed position wherein the leaflets (not shown) are captured and coapted. This is achieved by retraction of the stud 74 proximally relative to coupling member 19 so that the legs 68 of the actuation mechanism 58 apply an upwards force to the distal elements 18 which in turn rotate the distal elements 18 so that the engagement surfaces 50 again face one another. The released proximal elements 16 which are biased outwardly toward distal elements 18 are concurrently urged inwardly by the distal elements 18. The fixation device 14 may then be locked to hold the leaflets in this closed position as described below.

Figure 13:
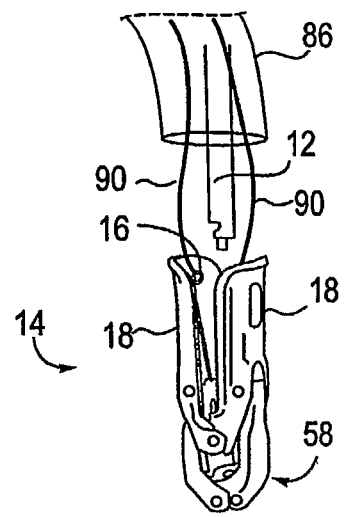

As shown in FIG. 13, the fixation device 14 may then be released from the shaft 12. As mentioned, the fixation device 14 is releasably coupleable to the shaft 12 by coupling member 19. FIG. 13 illustrates the coupling structure, a portion of the shaft 12 to which the coupling member 19 of the fixation device 14 attaches. As shown, the proximal element lines 90 may remain attached to the proximal elements 16 following detachment from shaft 12 to function as a tether to keep the fixation device 14 connected with the catheter 86. Optionally, a separate tether coupled between shaft 12 and fixation device 14 may be used expressly for this purpose while the proximal element lines 90 are removed. In any case, the repair of the leaflets or tissue may have been observed by non-invasive visualization techniques, such as echocardiography, to ensure the desired outcome. Then if the repair was not as desired, the fixation device 14 could be retrieved with the use of the tether or proximal element lines 90 so as to reconnect coupling member 19 with shaft 12.

The proximal element lines 90 may be elongated flexible threads, wire, cable, sutures or lines extending through shaft 12, looped through proximal elements 16, and extending back through shaft 12 to its proximal end. When detachment is desired, one end of each line may be released at the proximal end of the shaft 12 and the other end pulled to draw the free end of the line distally through shaft 12 and through proximal element 16 thereby releasing the fixation device.

Figure 14:
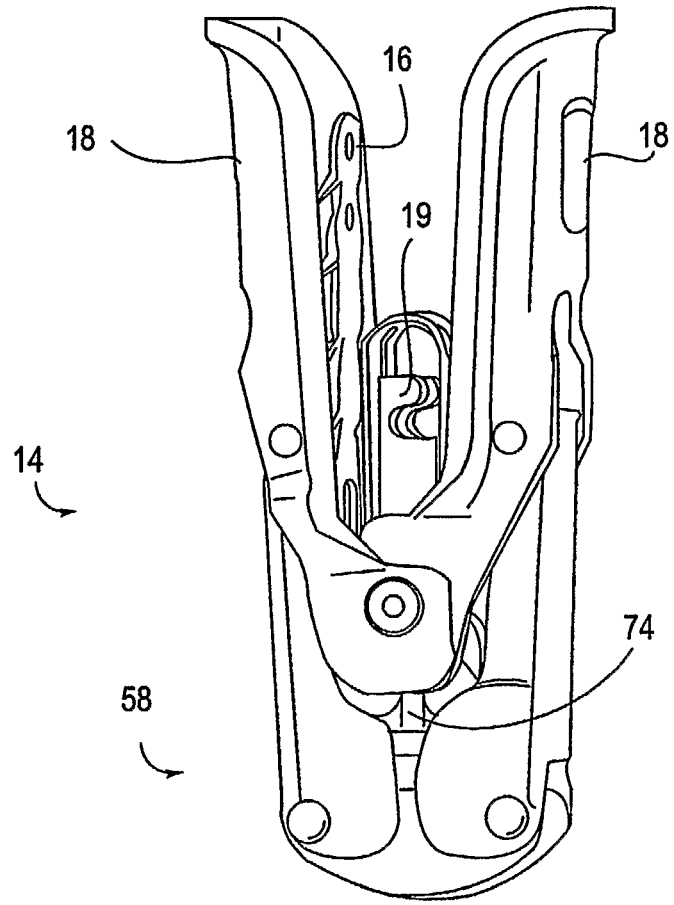

FIG. 14 illustrates a released fixation device 14 in a closed position. As shown, the coupling member 19 remains separated from the shaft 12 of the interventional tool 10 and the proximal elements 16 are deployed so that tissue (not shown) may reside between the proximal elements 16 and distal elements 18.

Instead of using a push-to-open, pull-to-close mechanism for opening and closing distal elements 18, a pull-to-open, push-to-close mechanism may also be used. For example, distal elements 18 may be coupled at their proximal ends to stud 74 rather than to coupling member 19, and legs 68 may be coupled at their proximal ends to coupling member 19 rather than to stud 74. In this example, when stud 74 is pushed distally relative to coupling member 19, distal elements 18 would close, while pulling on stud 74 proximally toward coupling member 19 would open distal elements 18.

B. Covering on Fixation Device

The fixation device 14 may optionally include a covering. The covering may assist in grasping the tissue and may later provide a surface for tissue ingrowth. Ingrowth of the surrounding tissues, such as the valve leaflets, provides stability to the device 14 as it is further anchored in place and may cover the device with native tissue, thus reducing the possibility of immunologic reactions. The covering may be comprised of any biocompatible material, such as polyethylene terephthalate, polyester, cotton, polyurethane, expanded polytetrafluoroethylene (ePTFE), silicone, or various polymers or fibers and have any suitable form, such as a fabric, mesh, textured weave, felt, looped or porous structure. Generally, the covering has a low profile so as not to interfere with delivery through an introducer sheath or with grasping and coapting of leaflets or tissue.

Figure 15A:
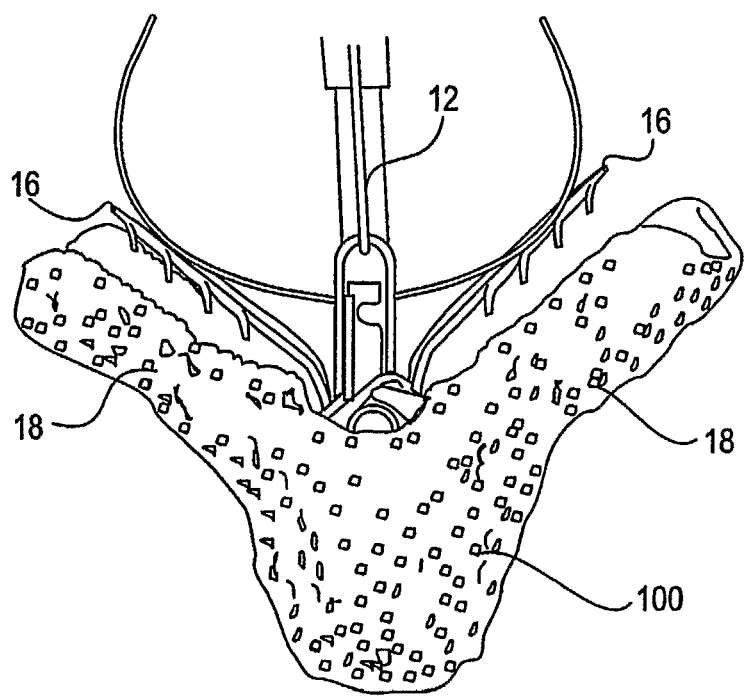
FIGS. 15A-15C illustrate a covering on the fixation device wherein the device is in various positions.
Figure 15B:
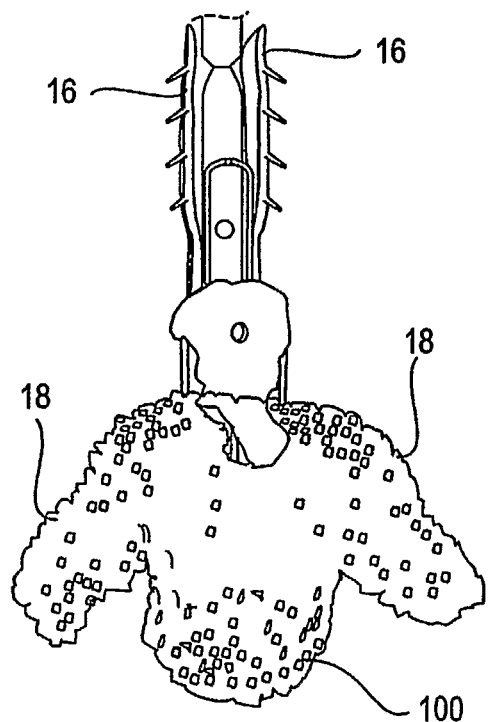
Figure 15C:
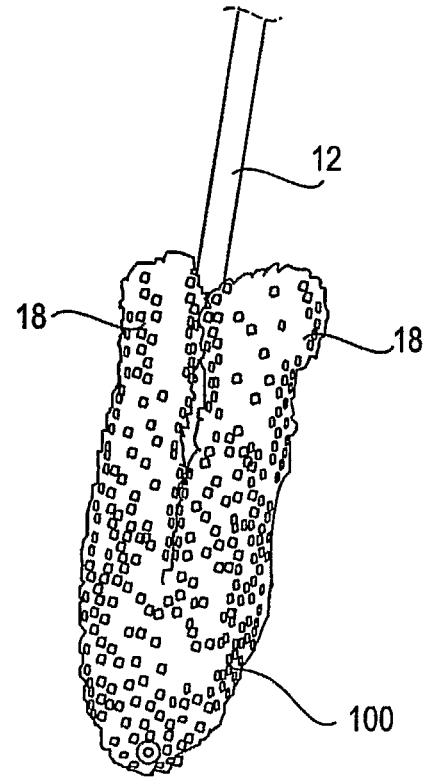

FIGS. 15A-15C illustrate a covering 100 on the fixation device 14 while the device 14 is in various positions. Additional description regarding such coverings may be found in PCT Publication No. WO 2004/103162, the disclosure of which is incorporated herein by reference in its entirety.

C. Locking Mechanism

Figure 16:
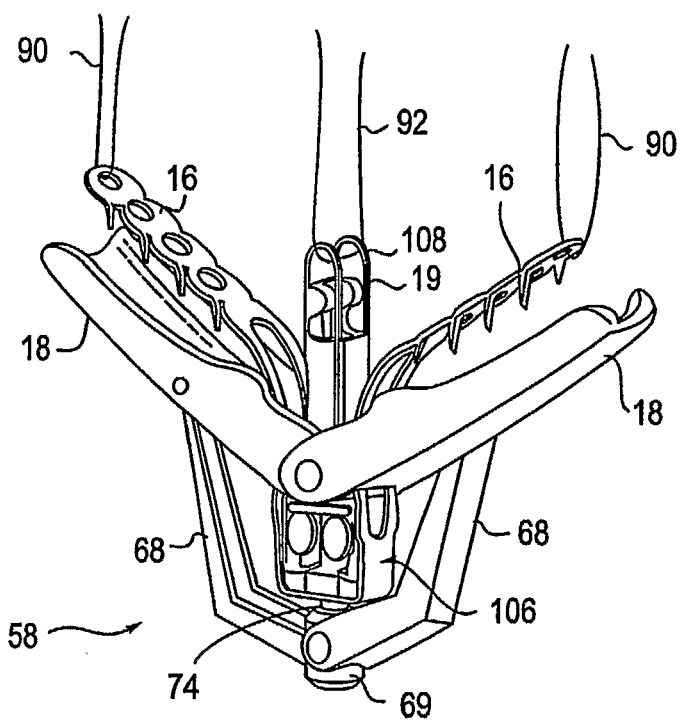
FIG. 16 illustrates a fixation device including proximal elements and a locking mechanism.

As mentioned previously, the fixation device 14 optionally includes a locking mechanism for locking the device 14 in a particular position, such as an open, closed or inverted position or any position therebetween. It may be appreciated that the locking mechanism includes an unlocking mechanism which allows the device to be both locked and unlocked. Various locking mechanisms can be used with the fixation device 14, such as those described in PCT Publication No. WO 2004/103162, which is incorporated herein by reference in its entirety. FIGS. 16-19 illustrate an exemplary locking mechanism 106. Referring to FIG. 16, the locking mechanism 106 is disposed between the coupling member 19 and the base 69 of the actuation mechanism 58. The base 69 is fixedly attached to the stud 74 which extends through the locking mechanism 106. The stud 74 is releasably attached to the actuator rod 64 which passes through the coupling member 19 and the shaft 12 of the interventional tool 10. The base 69 is also connected to the legs 68 of the actuation mechanism 58 which are in turn connected to the distal elements 18.

FIG. 16 also illustrates the proximal elements 16, which straddle the locking mechanism and join beneath the locking mechanism 106. The proximal elements 16 are shown supported by proximal element lines 90. The proximal elements 16 are raised and lowered by manipulation of the proximal element lines 90. In addition, lock lines 92 are shown connected with a release harness 108 of the locking mechanism 106. The lock lines 92 are used to lock and unlock the locking mechanism 106 as will be described below. The proximal element lines 90 and lock lines 92 may be comprised of any suitable material, typically wire, nitinol wire, cable, suture or thread, to name a few. In addition, the proximal element lines 90 and/or lock lines 92 may include a coating, such as parylene. Parylene is a vapor deposited pinhole free protective film which is conformal and biocompatible. It is inert and protects against moisture, chemicals, and electrical charge. The valve devices according to the present invention may similarly be coated with parylene or another coating.

Figure 17:
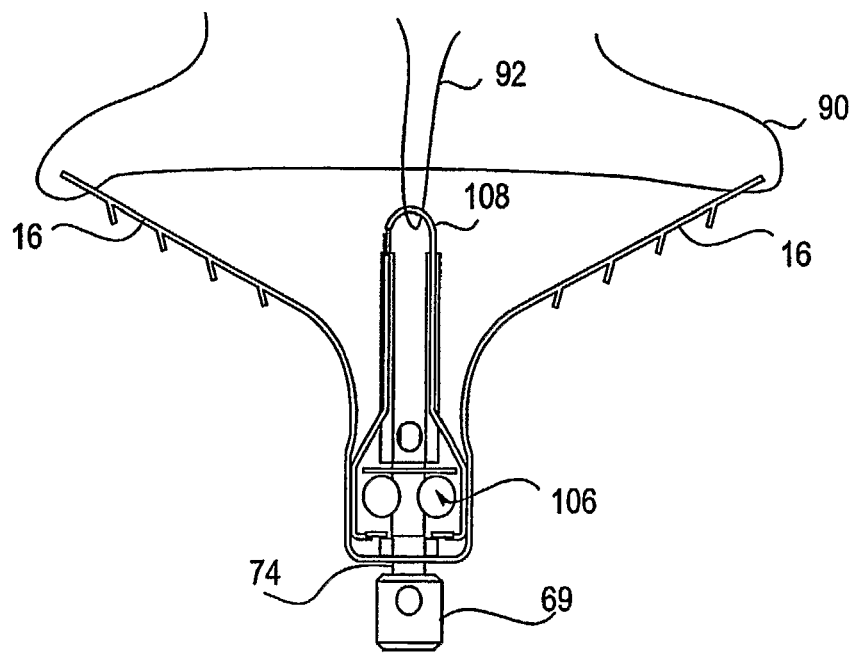
FIG. 17 provides a cross-sectional view of the locking mechanism of FIG. 16.

FIG. 17 provides a front view of the locking mechanism 106 of FIG. 16. However, here the proximal elements 16 are supported by a single proximal element line 90 which is through both of the proximal elements 16. In this arrangement both of the elements are raised and lowered simultaneously by action of a single proximal element line 90. Whether the proximal elements 16 are manipulated individually by separate proximal element lines 90 or jointly by a single proximal element line 90, the proximal element lines 90 may extend directly through openings in the proximal elements and/or through a layer or portion of a covering 100 on the proximal elements, or through a suture loop above or below a covering 100.

Figure 18:
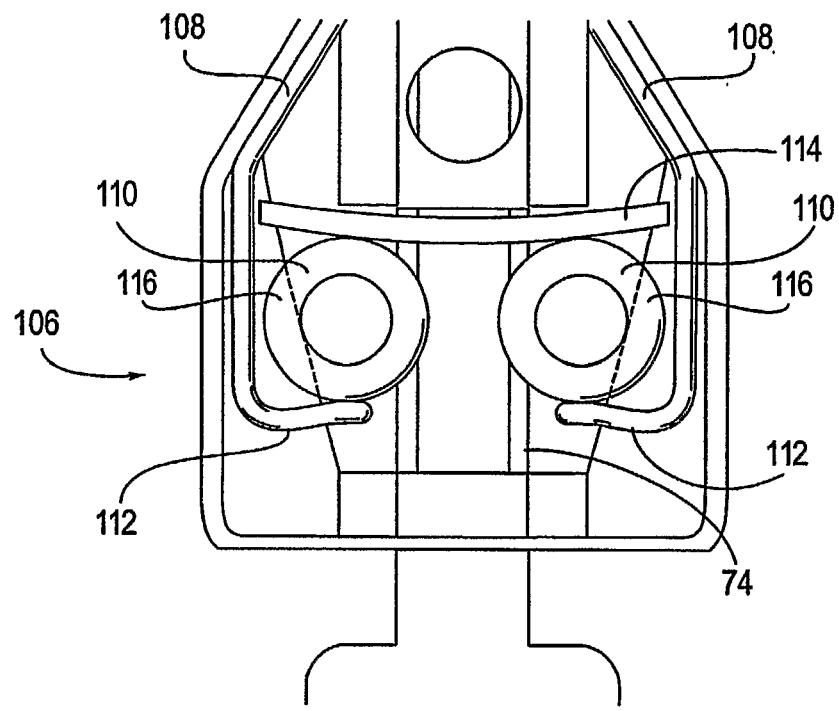
FIGS. 18-19 provide a cross-sectional view of the locking mechanism in the unlocked and locked positions respectively.
Figure 19:
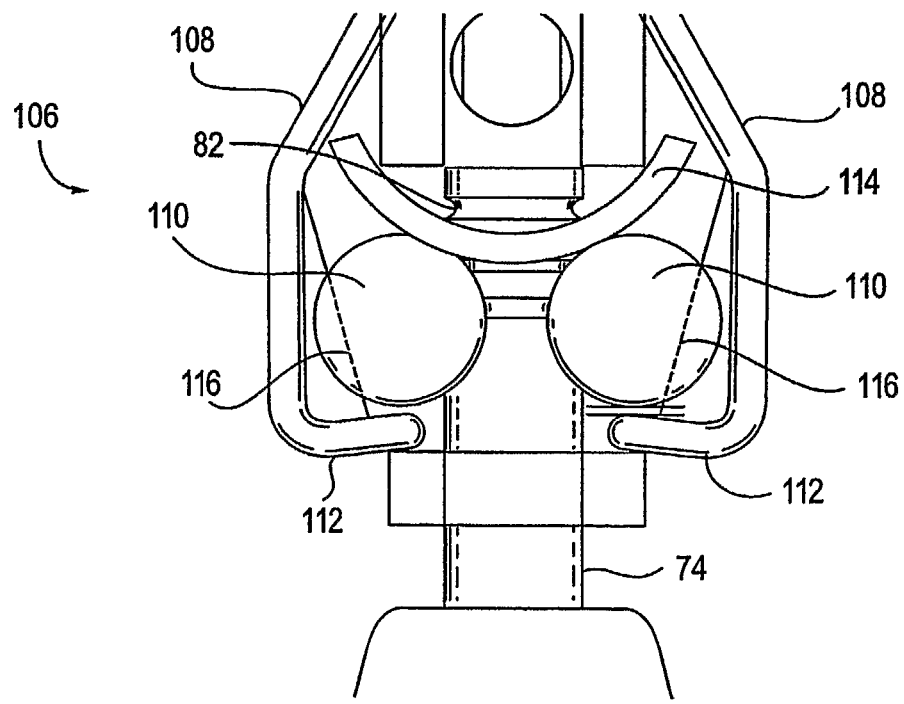

FIGS. 18-19 illustrate the locking mechanism 106 showing the locking mechanism 106 in the unlocked and locked positions respectively. Referring to FIG. 18, the locking mechanism 106 includes one or more wedging elements, such as rolling elements. In this example, the rolling elements comprise a pair of barbells 110 disposed on opposite sides of the stud 74, each barbell having a pair of generally cylindrical caps and a shaft therebetween. The barbells 110 and the stud 74 are preferably comprised of cobalt chromium or stainless steel, however any suitable material may be used. The barbells 110 are manipulated by hooked ends 112 of the release harness 108. When an upwards force is applied to the harness 108 by the lock line 92 (illustrated in FIG. 16), the hooked ends 112 raise the barbells 110 against a spring 114, as shown in FIG. 18. This draws the barbells 110 up along a sidewall or sloping surface 116 which unwedges the barbells 110 from against the stud 74. In this position, the stud 74 is free to move. Thus, when the lock line 92 raises or lifts the harness 108, the locking mechanism 106 is in an unlocked position wherein the stud 74 is free to move the actuation mechanism 58 and therefore the distal elements 18 to any desired position. Release of the harness 108 by the lock line 92 transitions the locking mechanism 106 to a locked position, illustrated in FIG. 19. By releasing the upwards force on the barbells 110 by the hooked ends 112, the spring 114 forces the barbells 110 downwards and wedges the barbells 110 between the sloping surface 116 and the stud 74. This restricts motion of the stud 74, which in turn locks the actuation mechanism 58 and therefore distal elements 18 in place. In addition, the stud 74 may include one or more grooves 82 or indentations which receive the barbells 110. This may provide more rapid and positive locking by causing the barbells 110 to settle in a definite position, increase the stability of the locking feature by further preventing movement of the barbells 110, as well as providing a tangible indication to the user that the barbell has reached a locking position. In addition, the grooves 82 may be used to indicate the relative position of the distal elements 18, particularly the distance between the distal elements 18. For example, each groove 82 may be positioned to correspond with a 0.5 or 1.0 mm decrease in distance between the distal elements 18. As the stud 74 is moved, the barbells 110 will contact the grooves 82; by counting the number of grooves 82 that are felt as the stud 74 is moved, the user can determine the distance between the distal elements 18 and can provide the desired degree of coaptation based upon leaflet thickness, geometry, spacing, blood flow dynamics and other factors. Thus, the grooves 82 may provide tactile feedback to the user.

The locking mechanism 106 allows the fixation device 14 to remain in an unlocked position when attached to the interventional tool 10 during grasping and repositioning and then maintain a locked position when left behind as an implant. It may be appreciated, however, that the locking mechanism 106 may be repeatedly locked and unlocked throughout the placement of the fixation device 14 if desired. Once the final placement is determined, the lock line 92 and proximal element lines 90 are removed and the fixation device is left behind.

Although FIGS. 18-19 describe an exemplary locking mechanism, it will be appreciated that alternative locking mechanisms may alternatively be employed.

As described herein, at a later stage, e.g., during a new endovascular procedure, the fixation device may be disabled or removed by cutting or otherwise partitioning the fixation device, or cutting the fixation device from tissue surrounding the installed device. For example, at such a later stage (e.g., weeks, months, or years after initial placement), it may no longer be practical to remove the device by unlocking the locking mechanism and disengaging the device from the leaflets (e.g., due to tissue growth around, into, and over the device).

Advantageously, such disablement or removal of the fixation device may be achieved through an endovascular procedure, without requiring open heart access.

D. Overview of Delivery Device

Figure 20:
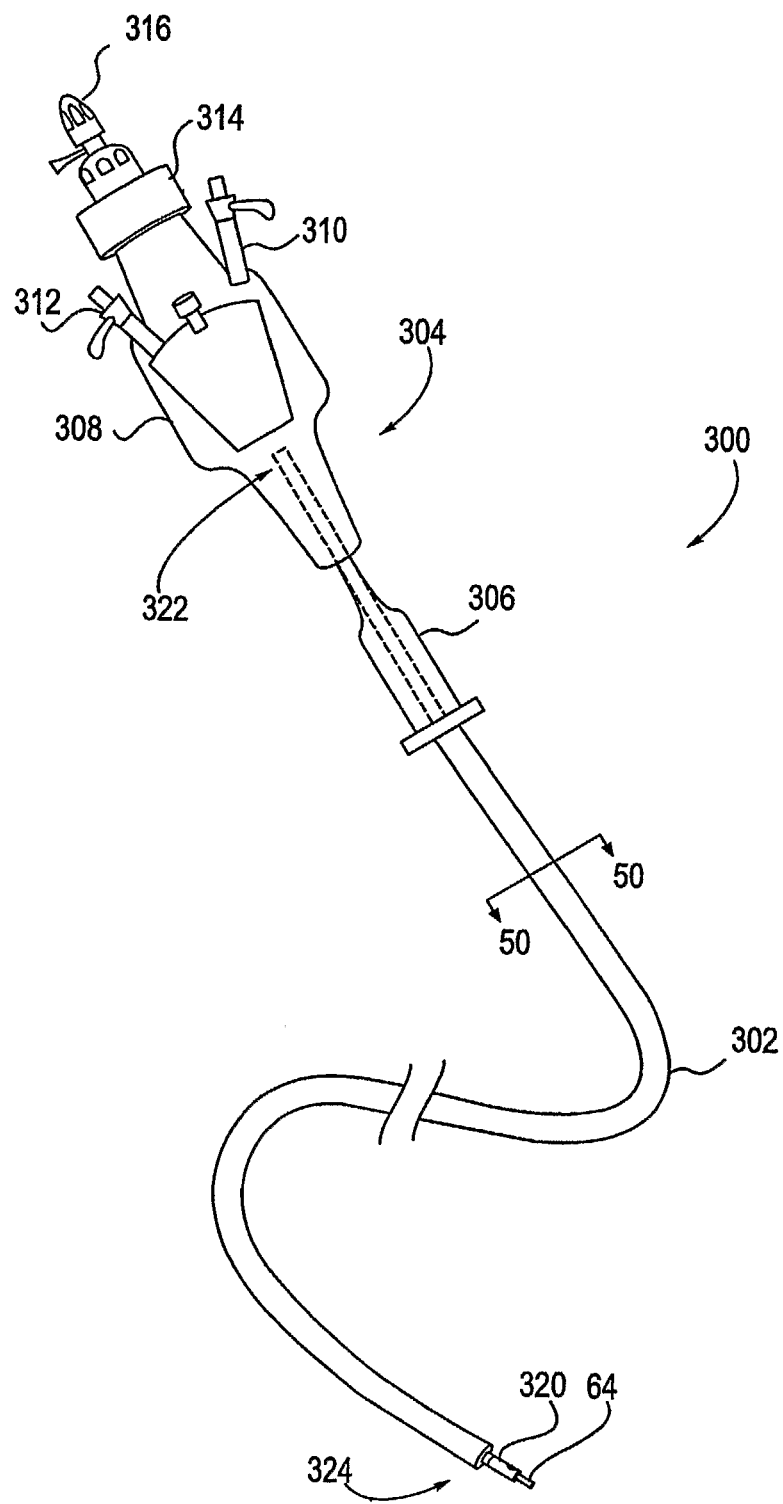
FIG. 20 illustrates a perspective view of an embodiment of a delivery catheter for a fixation device.

FIG. 20 provides a perspective view of an embodiment of a delivery device or delivery catheter 300 which may be used to introduce and position a fixation device as described above. The delivery catheter 300 includes a shaft 302, having a proximal end 322 and a distal end 324, and a handle 304 attached to the proximal end 322. A fixation device (not shown) is removably coupleable to the distal end 324 for delivery to a site within the body, typically for endovascular delivery to the mitral valve. Thus, extending from the distal end 324 is a coupling structure 320 for coupling with a fixation device. Also extending from the distal end 324 is an actuator rod 64. The actuator rod 64 is connectable with the fixation device and acts to manipulate the fixation device, typically opening and closing the distal elements. Such coupling to a fixation device is illustrated in FIG. 21.

The device may comprise a pair of distal elements and a pair of gripping elements as described herein. For example, each distal element and each gripping element may have a first end and a free end opposite the first end, the first ends of all of these elements being movably coupled together such that one distal element and one gripping element of the fixation device may be attached to the anterior leaflet, and one distal element and one gripping element of the fixation device may be attached to the posterior leaflet. The fixation device may further comprise a locking mechanism which locks at least the distal elements in place, wherein the locking mechanism includes a release harness, wherein applying tension to the release harness unlocks the locking mechanism. Additional embodiments are shown and described in a patent application filed the same day as the present application, U.S. patent application No. 14/216,787, filed Mar. 17, 2014, herein incorporated by reference in its entirety.

Figure 21:
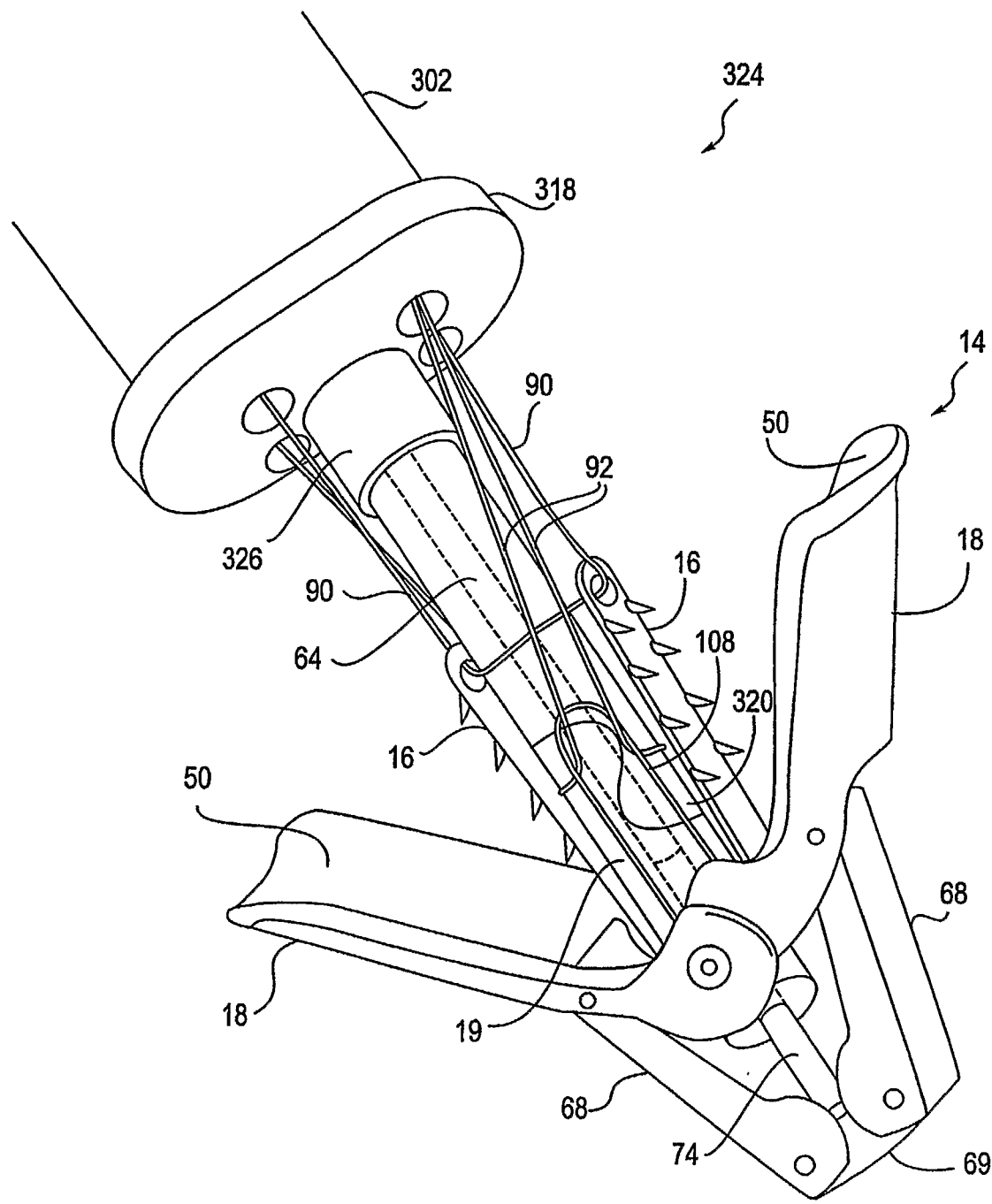
FIG. 21 illustrates an embodiment of a fixation device coupled to the distal end of a delivery catheter.

FIG. 21 illustrates an embodiment of a fixation device 14 coupled to the distal end 324 of the delivery catheter 300. The shaft 302 is shown having a nose 318 near its distal end 324. In this embodiment, the nose 318 has a flanged shape. Such a flanged shape prevents the nose 318 from being retracted into a guiding catheter or introducer as will be discussed in later sections. However, it may be appreciated that the nose 318 may have any shape including bullet, rounded, blunt or pointed, to name a few. Extending from the nose 318 is a compression coil 326 through which the coupling structure 320 and actuator rod 64 pass. The actuator rod 64 is coupleable, as shown, with the stud 74 of the fixation device 14. Such coupling is illustrated in FIG. 22.

Figure 22:
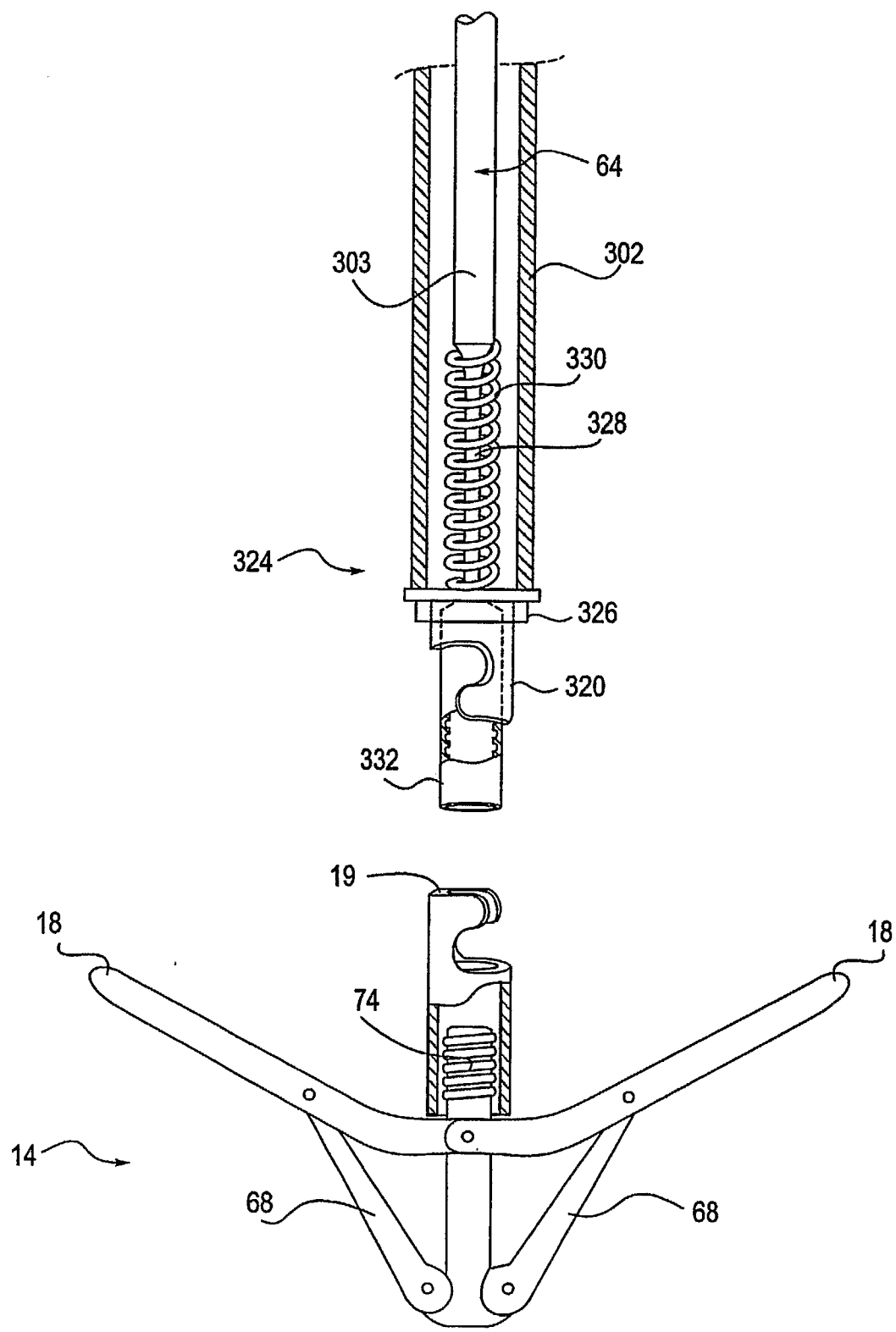
FIG. 22 illustrates a portion of the shaft of a delivery catheter and a fixation device which is coupleable with the catheter.

FIG. 22 illustrates a portion of the shaft 302 of the delivery catheter 300 and a fixation device 14 which is coupleable with the catheter 300. Passing through the shaft 302 is the actuator rod 64. In this embodiment, the actuator rod 64 comprises a proximal extremity 303 and a distal extremity 328, the distal extremity 328 of which is surrounded by a coil 330. The proximal extremity 303 is typically comprised of a material such as stainless steel, nitinol, or Elgiloy®, to name a few, and may have a diameter in the range of 0.010 in. to 0.040 in., preferably 0.020 in. to 0.030 in., more preferably 0.025 in., and a length in the range of 48 to 72 in. The distal extremity 328 may be tapered, is typically comprised of stainless steel, nitinol, or Elgiloy®, to name a few, and may have a diameter in the range of 0.011 to 0.025 in and a length in the range of 4 to 12 in. Such narrowing increases flexibility of the distal end 324 of the actuator rod 64. The actuator rod 64 further comprises a joiner 332 which is attached to the distal extremity 328. The joiner 332 is removably attachable with stud 74 of the fixation device 14. In this embodiment, the joiner 332 has internal threads which mate with external threads on the stud 74 of the fixation device 14. As described previously, the stud 74 is connected with the distal elements 18 so that advancement and retraction of the stud 74, by means of the actuator rod 64, manipulates the distal elements. Likewise, the coupling member 19 of the fixation device 14 mates with the coupling structure 320 of the catheter 300. Thus, the coupling member 19 and coupling structure 320 may function as previously described in relation to FIGS. 6A-6B.

Referring back to FIG. 21, the fixation device 14 may also include a locking mechanism which includes a release harness 108, as previously described in relation to FIGS. 16-19. Lock lines 92 are connected with the release harness 108 to lock and unlock the locking mechanism 106 as previously described. The lock lines 92 extend through the shaft 302 of the delivery catheter 300 and may connect with the release harness 108 in various arrangements as will be illustrated in later sections. Similarly, proximal element lines 90 extend through the shaft 302 of the delivery catheter 300 and connect with the proximal elements 16. The proximal elements 16 are raised and lowered by manipulation of the proximal element lines 90 as previously described. The proximal element lines 90 may connect with the proximal elements 16 in various arrangements.

Referring back to FIG. 20, the handle 304 attached to the proximal end 322 of the shaft 302 is used to manipulate the coupled fixation device 14 and to optionally decouple the fixation device 14 for permanent implantation. As described, the fixation device 14 is primarily manipulated by the actuator rod 64, proximal element lines 90 and lock lines 92. The actuator rod 64 manipulates the distal elements 18, the proximal element lines 90 manipulate the proximal elements 16 and the lock lines 92 manipulate the locking mechanism. The actuator rod 64 may be translated (extended or retracted) to manipulate the distal elements 18. This is achieved with the use of the actuator rod control 314 which will be described in later sections. The actuator rod 64 may also be rotated to engage or disengage the threaded joiner with the threaded stud 74. This is achieved with the use of the actuator rod handle 316 which will also be described in later sections. Further, the proximal element lines 90 may be extended, retracted, loaded with various amounts of tension or removed with the use of the proximal element line handle 312. The lock lines 92 may be extended, retracted, loaded with various amounts of tension or removed with the use of the lock line handle 310. The actuator rod handle 316, actuator rod control 314, proximal element line handle 312 and lock line handle 310 are all joined with a main body 308 within which the actuator rod 64, proximal element lines 90 and lock lines 92 are guided into the shaft 302. The handle 304 further includes a support base 306 connected with the main body 308. The main body 308 is slideable along the support base 306 to provide translation of the shaft 302. Further, the main body 308 is rotatable around the support base 306 to rotate the shaft.

E. Delivery Catheter Shaft

Figure 23:
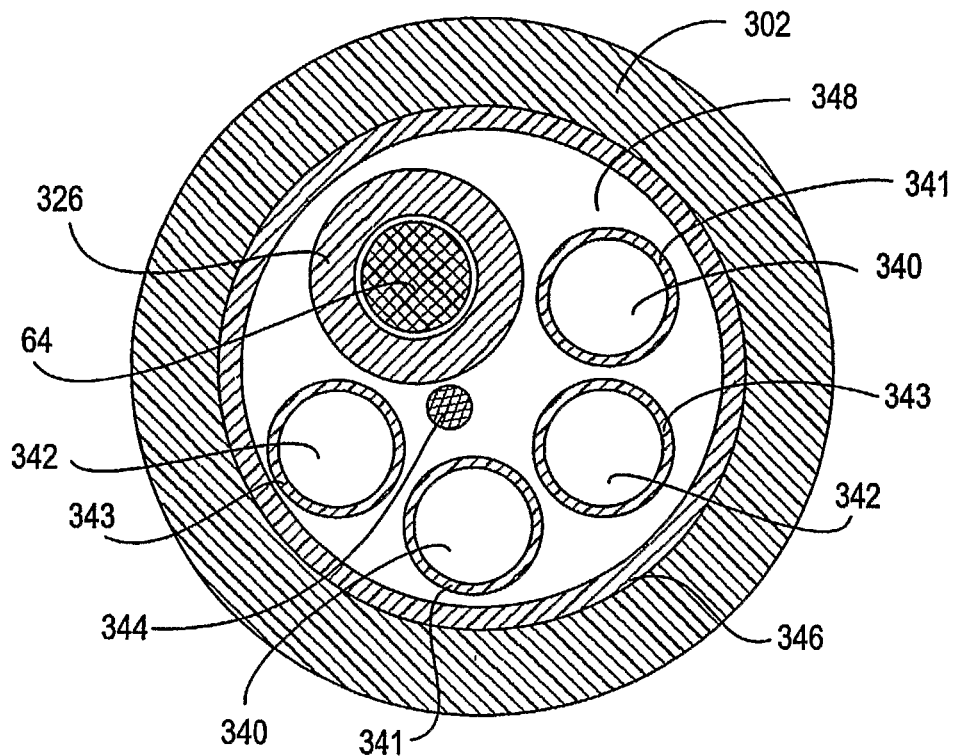
FIG. 23 is a cross-sectional view of the shaft of a delivery catheter.

FIG. 23 illustrates a cross-sectional view of the delivery catheter shaft 302 of FIG. 20. The shaft 302 has a tubular shape with inner lumen 348 and is comprised of a material which provides hoop strength while maintaining flexibility and kink resistance, such as a braided laminated material. Such material may include stainless steel braided or coiled wire embedded in a polymer such as polyurethane, polyester, Pebax, Grilamid TR55, and AESNO to name a few. To provide further support and hoop strength, a support coil 346 is disposed within the lumen 348 of shaft 302 as illustrated in FIG. 23. Similar materials and features may be employed in delivery catheters employed for delivery of the valve devices of the present invention.

Additional description regarding such a catheter may be found in PCT Publication No. WO 2004/103162, the disclosure of which is incorporated herein by reference in its entirety.

In addition, at least one lock line shaft 341 having a tubular shape may be present having a lock line lumen 340 through which lock lines 92 pass between the lock line handle 310 and the locking mechanism 106. The lock line shaft 341 extends through lumen 348 from the proximal end 322 to the distal end 324 of the shaft 302. Therefore, the lock line shaft 341 typically has a length in the range of 48 to 60 in., an inner diameter in the range of 0.016 to 0.030 in., and an outer diameter in the range of 0.018 to 0.034 in. The lock line shaft 341 may be comprised of a 304V stainless steel coil, however, other structures or materials may be used which provide kink resistance and compression strength.

Similarly, at least one proximal element line shaft 343 having a tubular shape may be present having a proximal element line lumen 342. Proximal element lines 90 pass through this lumen 342 between the proximal element line handle 312 and the proximal elements 16. Thus, the proximal element line shaft 343 extends through lumen 348 from the proximal end 322 to the distal end 324 of the shaft 302. Therefore, the proximal element line shaft 343 typically has a length in the range of 48 to 60 in., an inner diameter in the range of 0.016 to 0.030 in., and an outer diameter in the range of 0.018 to 0.034 in. The proximal element line shaft 343 may be comprised of a 304V stainless steel coil, however, other structures or materials may be used which provide kink resistance and compression strength.

It may be appreciated, however, that alternate shaft 302 designs may also be used. For instance, other shaft designs can be found in PCT Publication No. WO 2004/103162.

F. Lock Line Arrangements

Figure 24:
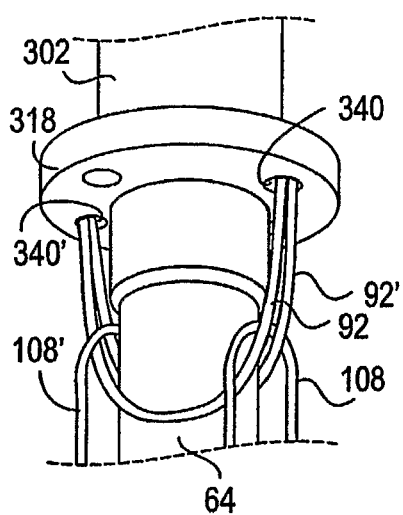
FIG. 24 illustrates various arrangements of lock lines engaging release harnesses of a locking mechanism.

As mentioned previously, when lock lines 92 are present, the lines 92 pass through at least one lock line lumen 340 between the lock line handle 310 and the locking mechanism 106. The lock lines 92 engage the release harnesses 108 of the locking mechanism 106 to lock and unlock the locking mechanism 106 as previously described. The lock lines 92 may engage the release harnesses 108 in various arrangements, examples of which are illustrated in FIG. 24. The two lock line lumens 340 are present within the shaft 302 of the delivery catheter 300 terminating at the nose 318. The lumens 340 are disposed on alternate sides of the actuator rod 64 so that each lumen 340 is directed toward a release harness 108. FIG. 24 illustrates an arrangement wherein two lock lines 92, 92' pass through a single lock line lumen 340 and are threaded through a release harness 108 on one side of the actuator rod 64 (the actuator rod 64 is shown without surrounding housing such as coupling structure, for clarity). The lock lines 92, 92' are then separated so that each lock line passes on an opposite side of the actuator rod 64. The lock lines 92, 92' then pass through the release harness 108' on the opposite side of the actuator rod 64 and continue together passing through a another single lock line lumen 340'. This lock line arrangement is the same arrangement illustrated in FIG. 21. Alternate lock line arrangements are possible, some of which can be found in PCT Publication No. WO 2004/103162, the disclosure of which is incorporated herein by reference in its entirety It may be appreciated that a variety of lock line arrangements may be used and are not limited to the arrangements illustrated and described above. The various arrangements allow the harnesses 108 to be manipulated independently or jointly, allow various amounts of tension to be applied and vary the force required for removal of the lock lines when the fixation device is to be left behind. For example, a single lock line passing through one or two lumens may be connected to both release harnesses for simultaneous application of tension.

G. Proximal Element Line Arrangements

Figure 25:
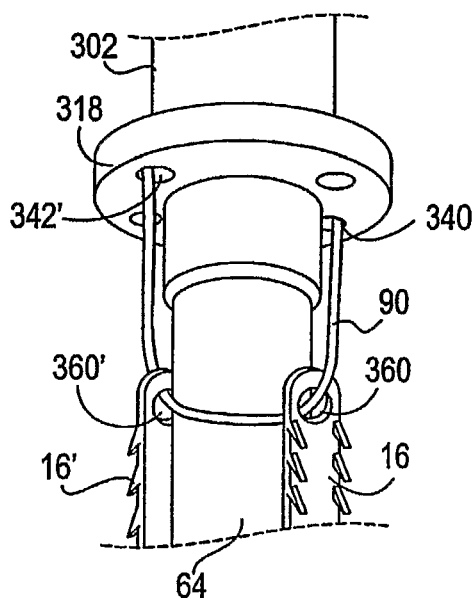
FIG. 25 illustrates various arrangements of proximal element lines engaging proximal elements of a fixation device.

As mentioned previously, when proximal element lines 90 are present, the lines 90 pass through at least one proximal element line lumen 342 between the proximal element line handle 312 and at least one proximal element 16. The proximal element lines 90 engage the proximal elements 16 to raise or lower the element 16 as previously described. The proximal element lines 90 may engage the proximal elements 16 in various arrangements, an example of which is illustrated in FIG. 25. The two proximal element line lumens 342 are present within the shaft 302 of the delivery catheter 300 terminating at the nose 318. The lumens 342 are disposed on alternate sides of the actuator rod 64 (the actuator rod 64 is shown without surrounding housing such as coupling structure, for clarity) so that each lumen 342 is directed toward a proximal element 16.

FIG. 25 illustrates an arrangement wherein one proximal element line 90 passes through a single proximal element line lumen 342. The proximal element line 90 is threaded through an eyelet 360 of a proximal element 16 on one side of the actuator rod 64, passes over the actuator rod 64 and is threaded through an eyelet 360' of another proximal element 16' on the other side of the actuator rod 64. The proximal element line 90 then passes through another single proximal element line lumen 342'. This proximal element line arrangement is the same arrangement illustrated in FIG. 21.

It may be appreciated that a variety of proximal element line arrangements may be used and are not limited to the arrangements illustrated and described above. For instance, and not by way of limitation, some alternate element line arrangements can be found in PCT Publication No. WO 2004/103162, the disclosure of which is incorporated herein by reference in its entirety. The various arrangements allow the proximal elements to be manipulated independently or jointly, allow various amounts of tension to be applied and vary the force required for removal of the proximal element lines when the fixation device is to be left behind. For example, a single proximal element line passing through one or two lumens in shaft 302 may be used for simultaneous actuation of both proximal elements.

H. Handle

Figure 26:
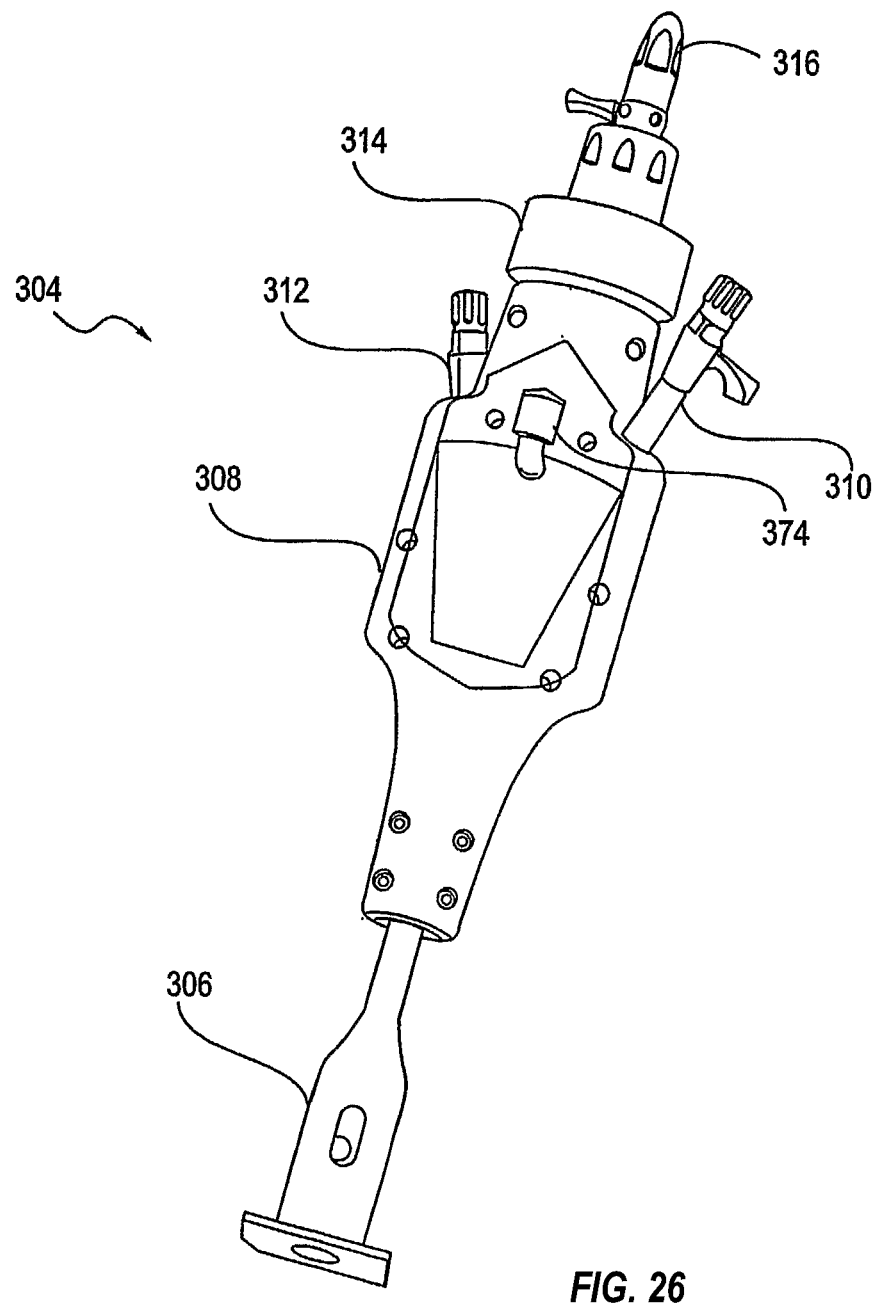
FIG. 26 illustrates a handle of a delivery catheter.

FIG. 26 illustrates a handle 304 of the delivery catheter 300. As mentioned previously, the actuator rod handle 316, actuator rod control 314, proximal element line handle 312 and lock line handle 310 are all joined with the main body 318. The handle 304 further includes a support base 306 connected with the main body 308. The main body 308 is slideable along the support base 306 to provide translation of the shaft 302 and the main body 308 is rotateable around the support base 306 to rotate the shaft.

It may be appreciated, that alternate handle 304 designs may also be used. For instance, further disclosure regarding handles can be found in PCT Publication No. WO 2004/103162, the disclosure of which is incorporated herein by reference in its entirety. For example, the handle may be designed to permit the manipulation of the lock lines and proximal element lines with the handle 304 or additional or different handles. Similarly, the handle may be designed to permit the manipulation of the actuator rod 64. A similar handle may be employed in delivery of the valve devices of the present invention.

I. Placement

To gain access to the mitral valve from the atrial side, an outer guide catheter may be tracked over a dilator and guidewire from a puncture in the femoral vein, through the inferior versa cava and into the right atrium. The outer guide catheter may be punctured through a fossa in the interatrial septum, into the left atrium. The outer guide catheter is then advanced through the fossa and curved by the primary curve so that the distal end is directed over the mitral valve. It may be appreciated that this approach serves merely as an example and other approaches may be used, such as through the jugular vein, femoral artery, port access or direct access, to name a few. For example, access to the heart may be accomplished through a thoracotomy or similar procedure involving, for example, trans-apical access to the left ventricle. Positioning of the distal end over the mitral valve may be accomplished by precurvature of the outer guide catheter, wherein the catheter assumes this position when the dilator and guidewire are retracted, and/or by steering of the outer guide catheter to the desired position.

An inner guide catheter is advanced through the central lumen of the outer guide catheter and the distal end is positioned so that the central lumen is directed toward the target tissue, the mitral valve MV. In particular, the central lumen is to be directed toward a specific area of the mitral valve, such as toward the opening or openings between the valve leaflets or a device implanted in the mitral valve.

To gain access to the mitral valve from the ventricular side, an outer guide catheter may be tracked over a dilator and guidewire from a puncture in the femoral artery, through the aorta and into the left ventricle. The outer guide catheter is then advanced through the left ventricle so that the distal end is directed under the mitral valve. It may be appreciated that this approach serves merely as an example and other approaches may be used, such as through the jugular vein, femoral vein, port access or direct access, to name a few. For example, access to the heart may be accomplished through a thoracotomy or similar procedure involving, for example, trans-apical access to the left ventricle. Positioning of the distal end under the mitral valve may be accomplished by precurvature of the outer guide catheter, wherein the catheter assumes this position when the dilator and guidewire are retracted, and/or by steering of the outer guide catheter to the desired position. Any of the above described endovascular access procedures may similarly be used when disabling or removing a previously installed fixation device.

An inner guide catheter is advanced through the central lumen of the outer guide catheter and the distal end is positioned so that the central lumen is directed toward the target tissue, the mitral valve MV. In particular, the central lumen is to be directed toward a specific area of the mitral valve, such as toward the opening between the valve leaflets.

Any of the above described endovascular access procedures may similarly be used when delivering a valve device according to the present invention. For example, where no fixation device is installed, or the fixation device has been disabled, a valve device may be delivered using an antegrade approach, through the atrium. Where a fixation device is already attached to the mitral valve, a retrograde approach may be employed. For example, the valve device may be introduced through the ventrical side and anchored to the body of the fixation device 14 (e.g., legs 68 and adjacent structure).

III. Double Orifice Valve Devices

Sometimes, after installation of a fixation device in the heart, there still exists an unacceptable degree of regurgitation, mitral stenosis may be present, or there may be another issue not fully addressed by the fixation device. In such instances, it may be desirable to create a double orifice replacement valve that preserves the existing valvular and sub-valvular apparatus of the mitral valve (i.e., without cutting away or removing any or substantial portions of the mitral valve apparatus). Such a replacement valve may address mitral regurgitation, mitral stenosis, or another issue. Such a valve device may be anchored to an existing edge-to-edge fixation device (e.g., such as MitraClip®), or onto the mitral valve leaflets in a manner that is similar to how such a fixation device is secured to the mitral valve leaflets (e.g., see FIGS. 3A-4). In either case, the valve device becomes anchored (e.g., directly or indirectly) to the mitral valve, and allows deployment of a replacement valve that preserves and augments the existing mitral valve structure to provide a valve with improved function (e.g., reduced regurgitation, etc.). Thus, such devices and methods allow valve replacement for bi-leaflet mitral valves previously repaired with such a fixation device. The valve device and associated methods advantageously allow percutaneous, minimally invasive delivery and replacement. Although described principally in terms of a double orifice valve that replaces valve apparatus at both orifices of an edge-to-edge repaired mitral valve, it will be appreciated that the valve devices and related methods may provide valve replacement for only one of the two orifices (e.g., if one of the orifices is performing acceptably, etc.), such that the methods, valve devices, and related systems are not limited to double orifice implementations.

An exemplary orifice valve device may include an anchoring and manifold assembly, a peripheral ring anchoring system, and a trap door valve. The anchoring and manifold assembly may be coupleable to a delivery catheter (e.g., so that the valve device can be delivered through such a delivery catheter). Any of the above described coupling mechanisms (e.g., those described in conjunction with FIGS. 5A-6B) for coupling to a delivery catheter may be suitably employed. The anchoring and manifold assembly includes means for anchoring the valve device to the mitral valve or to a fixation device that is attached to the mitral valve.

The peripheral ring anchoring system may be secured to the anchoring and manifold assembly, and may include one or more (e.g., two) expandable anchoring rings that can be expanded within the orifice(s) of the mitral valve so as to surround the annular perimeter of the orifice. The peripheral ring anchoring system may further include a helical suture that is helically disposable about each expandable anchoring ring that secures the expandable ring to leaflet tissue adjacent the perimeter of the orifice of the mitral valve. The trap door valve of the valve device may be hingedly secured to the anchoring and manifold assembly, the peripheral ring anchoring system, or both. The trap door valve may include a trap door body that selectively seals against the expandable anchoring ring that extends around the perimeter of the orifice of the mitral valve (i.e., closing the orifice) during the systole portion of the cardiac cycle. The trap door body selectively unseals relative to the expandable anchoring ring so as to open the orifice of the mitral valve during the diastole portion of the cardiac cycle.

Figure 27:
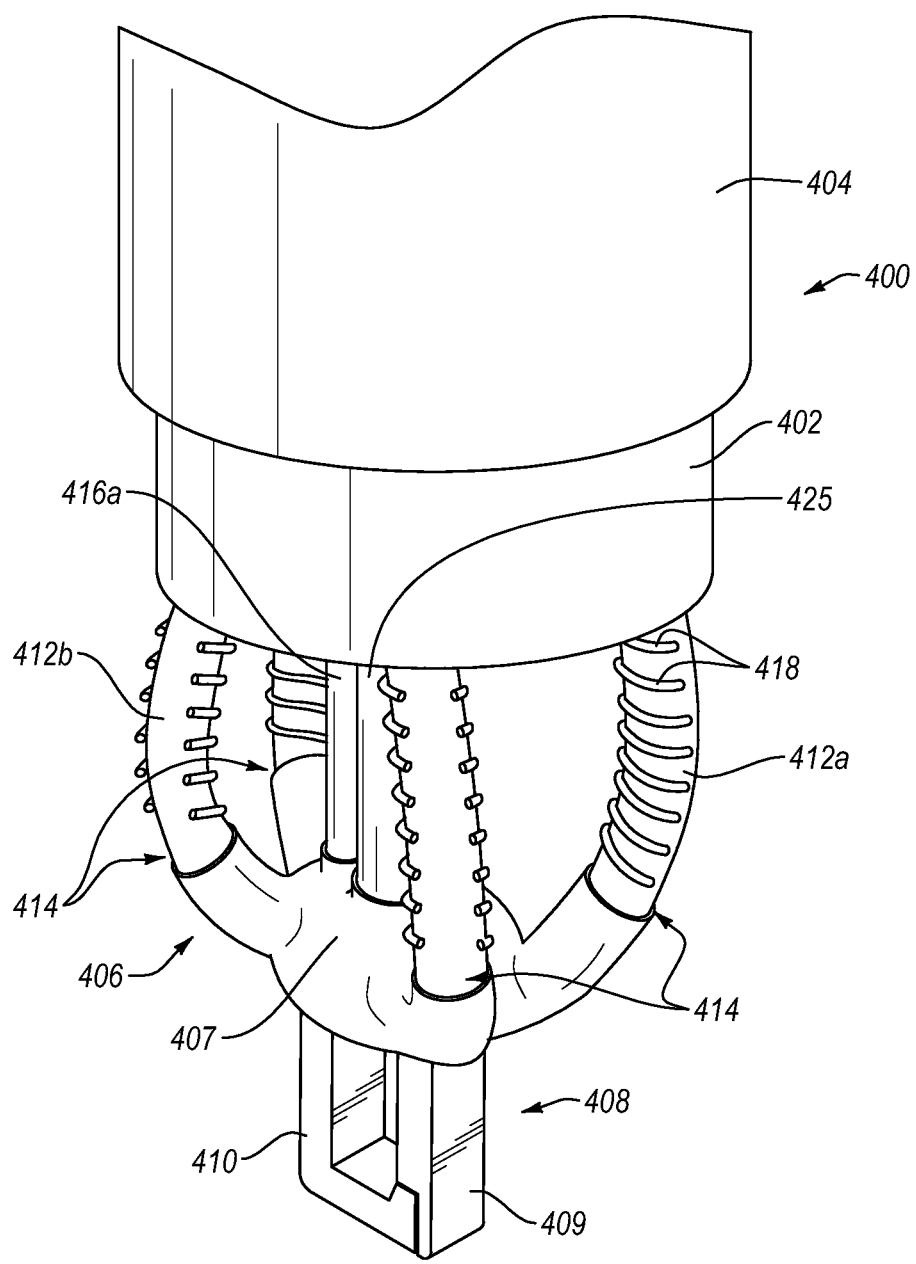
FIG. 27 illustrates an exemplary double orifice valve device for attachment to a mitral valve, the valve device being deployed from a delivery catheter.

FIG. 27 illustrates an exemplary double orifice valve device 400 being delivered through a delivery catheter 402 disposed within a guide catheter 404. FIG. 28A shows the rings of device 400 in an unfolded configuration. The trap door valve, including trap door body is not shown in FIGS. 27-28C for purposes of more clearly showing the foldable and expandable rings. The trap door valve and trap door body are shown and described below in conjunction with FIGS. 32A-33.

Device 400 includes an anchoring and manifold assembly 406 that provides means for anchoring the valve device 400 to the mitral valve or to a fixation device (e.g., fixation device 14) that may be attached to the mitral valve. For example, device 400 may include a capture or latch structure, such as basket 408 including a selectively movable arm 410 for opening and closing the basket 408 so as to selectively capture at least a portion of a fixation device that is attached to the mitral valve. FIG. 28B shows basket 408 in an open configuration, while FIG. 28C shows basket 408 in a closed configuration, capturing at least a portion of fixation device 14 therein. Movable arm 410 may include a hinge 411 (FIG. 28A), which may be selectively activated (e.g., by pulling a lock line, push rod actuation, or any other suitable mechanism) to open basket 408. Once basket 408 is closed (e.g., by pushing or releasing a lock line back down), it may lock in place, securing device 400 about fixation device 14.

Illustrated basket 408 includes two arms (e.g., 410 and 409), at least one of which is movable relative to the other. In the illustrated embodiment, movable arm 410 may be generally L-shaped, including a transverse foot portion that locks or latches against or relative to opposite arm 409. Arm 409 is illustrated as being substantially straight, and including a recess at its free end for receiving a corresponding protruding portion of the transverse foot portion of L-shaped arm 410. A latching or locking mechanism may be provided between the recess at the free end of arm 409 and the corresponding protruding portion of arm 410, to lock the two arms together. Alternatively, a locking mechanism may be disposed adjacent hinge 411 that selectively locks arm 410 in a closed position.

Arms 410 and 409 may be in the closed position (e.g., FIG. 27) during delivery through catheter 404 and 402, and may be changed to the open position once device 400 has at least partially exited delivery catheter 402 (e.g., so as to occupy minimal width or space while in delivery catheter 402). While basket 408 is described above, it will be appreciated that various other mechanisms for capturing at least a portion of a fixation device installed within the mitral valve will be apparent to one of skill in the art, any of which may be suitable for use. Non-limiting examples include magnetic retention systems, other mechanical structures for capturing or locking to a portion of the fixation device, etc.

Figure 28D:
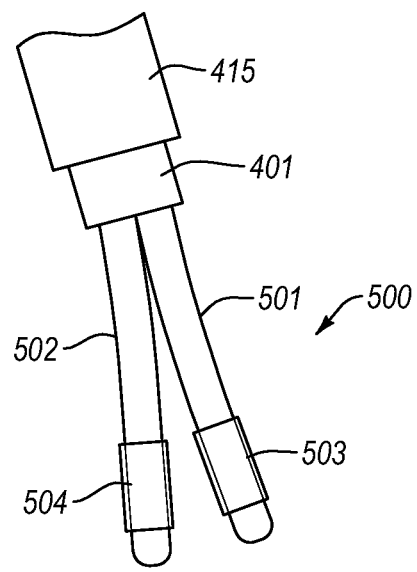
FIG. 28D illustrates a double orifice balloon valvuloplasty device.

FIG. 28C shows a fixation device 14 captured within basket 408. FIG. 28D shows a close up of fixation device 14, which is similar to that described above in conjunction with FIGS. 3A-25, but which includes a more easily accessible release harness 108". Release harness 108" may extend beyond the free ends of the proximal elements 16, distal elements 18, or both, as shown, when the device is in a closed and locked position. Such a fixation device is described in further detail in U.S. patent application No. 14/216,787,filed Mar. 17, 2014, and herein incorporated by reference in its entirety.

In another embodiment, device 400 may include a clip or grasping type mechanism such as that described above relative to fixation device 14 (e.g., distal and proximal elements 16, 18 that grasp opposing leaflets LF of the mitral valve MV, as seen in FIGS. 3A-3C). Such an embodiment allows valve device 400 to latch directly onto the leaflets LF of the mitral valve MV, rather than anchoring device 400 to the fixation device, which in turn is latched onto leaflets LF. Such grasping distal and proximal elements 16, 18 are described in detail above, and shown in FIGS. 3A-3C. For example, the clip mechanism may grasp opposite sides of the mitral valve leaflets along segments A2 and P2, pulling them together, as shown in FIG. 4.

An appropriately configured handle at the proximal end of guiding catheter 404 may be provided for opening and closing basket 408, as well as for all other functions controlled by the practitioner during installation of device 400 (e.g., initiating expansion of rings 412a, 412b with saline, for withdrawal of saline through line 416b, for advancement of suture 420, for introduction of hardenable polymer or other material into rings 412a, 412b, deployment of trap door body of trap door valve 426, etc.).

Device 400 further includes at least one expandable anchoring ring (e.g., rings 412a and 412b) secured to the anchoring and manifold assembly 406. Rings 412a and 412b may comprise flexible, hollow tubular rings that are sufficiently flexible during delivery to allow them to be folded upon one another and stored within delivery catheter 402. For example, as seen in FIGS. 27 and 28A, rings may be folded approximately 90° in their folded state (FIG. 27) relative to their unfolded (FIG. 28) state. Rings 412a, 412b, as well as trap door body 428 (FIG. 32A) are initially flexible and foldable so as to allow these structures to be folded upon themselves, and be sufficiently small for delivery through a delivery catheter. For example, rings 412a, 412b may fold towards the proximal end of the delivery catheter 402, so that the anchoring and manifold assembly 406 may be first to emerge from the distal end of delivery catheter 402. Rings 412a and 412b may be formed of any suitable flexible material. In an embodiment, they may comprise a polymer or plastic material, e.g., that may be coated with polyester or another coating material. Trap door body 428 may similarly be formed of a flexible sheet-like material, e.g., polyethylene terephthalate, polyester, polyurethane, expanded polytetrafluoroethylene (ePTFE), or various other polymers.

Ends 414 of rings 412a, 412b may be coupled to anchoring and manifold assembly 406. Assembly 406 may include a manifold 407 connectable to delivery catheter 402 through distribution lines 416a, 416b for introducing a fluid into rings 412a, 412b, so as to expand the rings 412a, 412b, as they are positioned within the orifice(s) of the mitral valve. Lines 416a, 416b may allow delivery and subsequent withdrawal of saline or other fluid into expandable rings 412a, 412b, as well as a hardenable polymer or other hardenable fluid material delivered once rings 412a, 412b have been secured in place.

Expansion of rings 412a, 412b with saline or a similar material allows rings 412a, 412b to be expanded to fit the particular contours of each orifice. The rings 412a, 412b may thereafter be secured in place using a suture or other securing mechanism. Once expanded and secured within the orifices by suture or other mechanism, a hardenable fluid (e.g., a curable polymer) may then be injected into rings 412a, 412b using lines 416a, 416b as the saline or other fluid employed for initial expansion of rings 412a, 412b is withdrawn through the same distribution system. For example, line 416a may serve as an "inlet" for introduction of fluid into both rings 412a and 412b, while line 416b may serve as an "outlet" for withdrawal of fluid from both rings 412a and 412b. Fluid communication may thus be provided between line 416a and rings 412a and 412b, and between line 416b and rings 412a and 412b. Such fluid communication may be provided through manifold 407, so as to allow selective introduction of saline or other expanding fluid, followed saline withdrawal and introduction of the hardenable fluid.

Before or during such a procedure where such an orifice valve replacement device is installed, it may be desirable to prepare the orifices by performing balloon valvuloplasty in one or both orifices (e.g., substantially simultaneously). FIG. 28E illustrates a device for performing such a procedure. A balloon valvuloplasty assembly 500 may comprise two arms 501 and 502 which are configured so that, once the balloon valvuloplasty assembly 500 is advanced out of an outer guide catheter 415, the two arms 501 and 502 separate at an appropriate distance so that one arm 501 can be advanced into one orifice of the mitral valve double orifice structure and the other arm 502 can be advanced into the other orifice. Arms 501 and 502 may each have a balloon 503 and 504 disposed at or near a distal end of each respective arm, and may be attached to a delivery catheter 401. Balloons 503 and 504 can be inflated when the arms 501 and 502 are advanced to a position within the orifices. Such a balloon system may also be used when expanding the peripheral ring anchoring system of the present invention within the orifice(s) of the mitral valve. Where balloons are employed either to expand the orifice(s) or to expand the peripheral ring anchoring system, a balloon may be deployed within one orifice at a time, if desired. This may be particularly advantageous as the valve is not completely blocked due to the presence of the other orifice of the mitral valve. For example, a practitioner may carefully expand one orifice without needing to "rush", as such a one-at-a-time procedure does not completely block the mitral valve, thus not blocking diastolic filling of the left ventricle. The inflation of the balloons 503 and 504 may be done by methods known in the art, and can be controlled by an appropriately configured handle located at the proximal end of the outer guide catheter 415.

Figure 29:
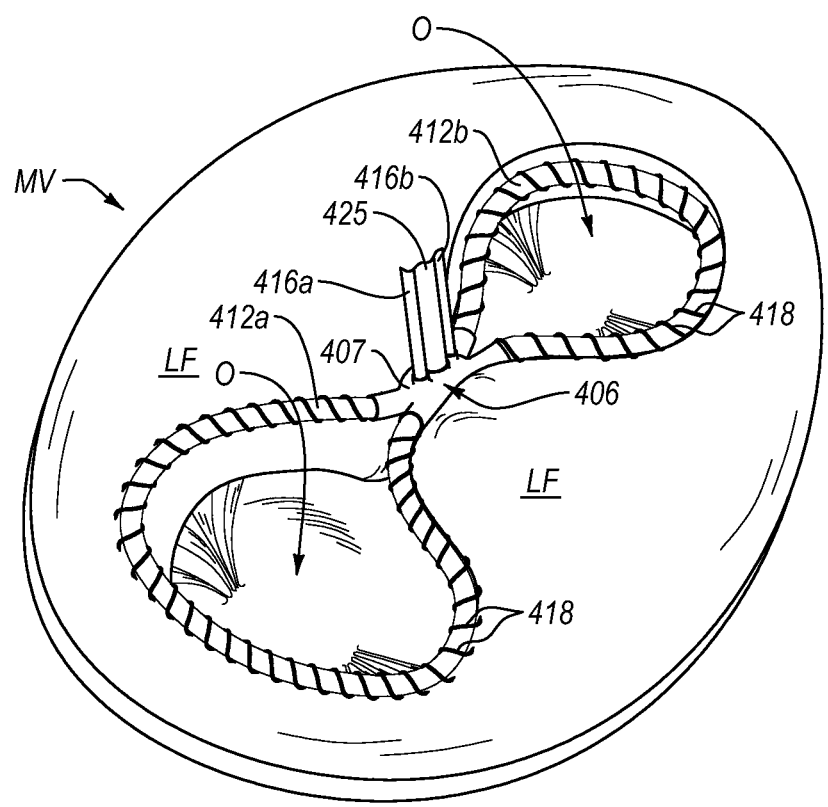
FIG. 29 illustrates a mitral valve over which the valve device of FIGS. 28A-28C has been anchored, and in which the peripheral anchoring rings have been expanded within both orifices of the mitral valve.

Turning to FIG. 29, once orifices O are prepared, saline or a similar expansion fluid allows rings 412a and 412b to be expanded within the respective annulus of each orifice of the mitral valve as the rings are positioned for their securement within the orifices O. Delivery of a hardenable polymer or other material may be achieved after the rings 412a, 412b have been sutured or otherwise secured within the respective orifices. Providing such a hardenable material within rings 412a, 412b provides increased rigidity to the filled and expanded rings, and may further aid in plugging any voids that may otherwise cause perivalvular leaks. For example, the hardened polymer or other material within rings 412a, 412b may create a tighter seal (as compared to that provided by saline filled rings) between the tubular rings 412a, 412b and the annulus of the mitral valve. It may also provide relatively rigid support in the region of the commissures of the mitral valve for anchoring and sealing of the far ends of each trap door body of the valve structures. The commissures refer to that portion of the mitral valve disposed along its major axis, on either end of the valve (e.g., opposite ends of line C in FIG. 4). As with the other above described functions, an appropriately configured handle at the proximal end of guiding catheter 404 may be provided for initiating expansion of rings 412a, 412b with saline, for withdrawal of saline through line 416b, and for introduction of hardenable polymer or other material into rings 412a, 412b.

FIG. 29 shows rings 412a, 412b situated within the annulus or perimeter of each orifices O of mitral valve MV, with the rings positioned against the perimeter or annulus of orifices O bounded by leaflets LF. When rings 412a, 412b are filled with saline, this allows creation of a snug fit around the perimeter of the double orifice lining of the mitral valve leaflets LF to allow as much area as possible for the subsequently deployed trap door valve, as well as to prevent or minimize perivalvular leaks, between the tissue of the mitral valve and structures of the valve 400. For example, rings 412a, 412b may press tightly against the annulus of the mitral valve, preventing blood seepage therebetween. This tightly pressing relationship may be further sealed once rings 412a, 412b are injected with a hardenable polymer material.

Figure 30:
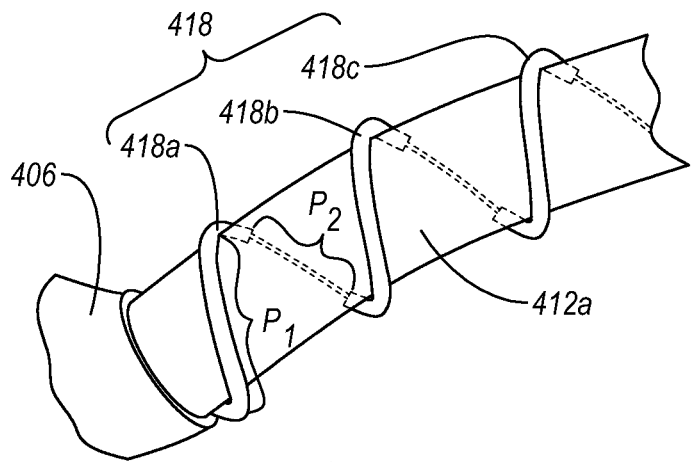
FIG. 30 illustrates a close-up schematic view of a portion of the anchoring ring including a discontinuous helical suture conduit through which a helical suture may be advanced so as to secure the anchoring ring to leaflet tissue around the perimeter of the orifice of the mitral valve.

Once positioned within orifice O where desired, the position may be secured by suturing rings 412a, 412b in place. As seen in FIGS. 29 and 30, each ring 412a, 412b may include a helical suture conduit 418 that is attached to anchoring ring 412a, 412b. Conduit 418 may be discontinuous, as perhaps best seen in FIGS. 30 and 31A-31B, so as to extend about a portion of the perimeter of the anchoring ring that is not disposed adjacent to the leaflet tissue LF. As shown, perimeter portion P1 (outwardly exposed portions of ring 412a) includes conduit 418, while portion P2 (the backside of ring 412a, adjacent leaflets LF) does not include conduit. As such, conduit 418 includes multiple, discontinuous portions 418a, 418b, 418c, etc. that are helically aligned with one another, so that as a screwing helical suture 420 is advanced through a first conduit portion 418a, it exits an end of portion 418a, adjacent leaflet tissue LF, where it can penetrate tissue LF as it traverses perimeter portion P2, and thereafter reenters conduit 418, into second portion 418b. The screwing helical suture is thus able to advance through one conduit portion, into tissue LF, into an adjacent, next conduit portion, and so on, all the way around ring 412a or 412b. One suture may be provided for each ring. Advancement of helical suture 420 may be controlled at an appropriately configured handle at the proximal end of catheters 402, 404. Helical suture 420 may be pre-shaped into its helical shape, e.g. as a suture wire, so as to facilitate its exit from one conduit portion, penetration through tissue LF on the same helical trajectory, and its re-entry into the next, adjacent conduit portion. Conduit portions 418 may include an inside diameter that is somewhat larger than the diameter of suture wire 420, so as to facilitate its introduction therein.

Figure 31A:
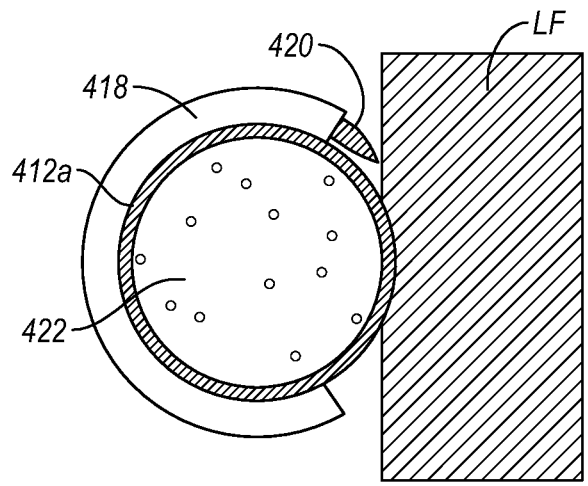
FIGS. 31A-31B illustrate cross-sectional schematic views showing how the helical suture may be advanced through a first portion of the discontinuous helical suture conduit, penetrating leaflet tissue adjacent the anchoring ring, and entering a second portion of the suture conduit so as to secure the anchoring ring to the leaflet tissue.
Figure 31B:
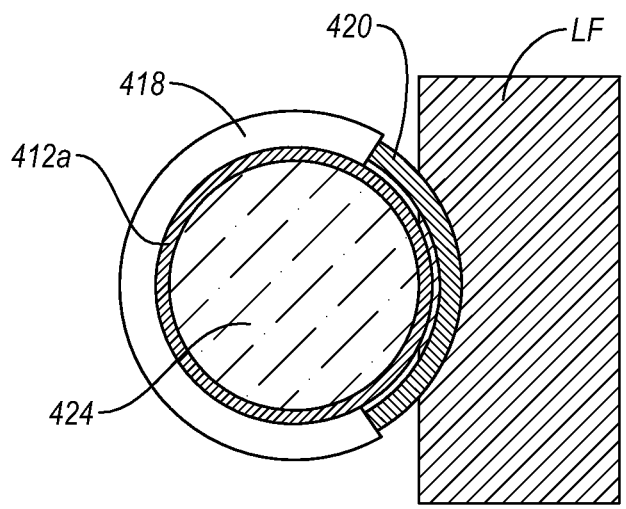

As further illustrated in FIGS. 31A-31B, during advancement of helical suture 420, rings 412a and 412b may be filled with saline 422 (FIG. 31A), while once helical suture 420 has been fully advanced around rings 412a and 412b, the saline 422 may be withdrawn, and replaced with a hardenable polymer or other hardenable material 424, (FIG. 31B) which may harden or cure to provide a degree of rigidity that is greater than that provided by the saline filled ring 412a, 412b. Such increased rigidity provides an anchor for the subsequently deployed trap door valve, which may be hingedly attached to rings 412a, 412b and or anchoring/manifold assembly 406 (e.g., in the A2/P2 region of the mitral valve), while also providing excellent relatively rigid support to securely anchor valve device 400 adjacent the oppositely disposed commissures of the mitral valve. Polymer filled rings 412a, 412b further aid in plugging any gaps that may exist around the helical screwing suture, also preventing or minimizing any perivalvular leaks resulting therefrom. Any suitable hardenable polymer or other hardenable material (e.g., chemically initiated curable polymer) may be employed (e.g., silicones, acrylates, methacrylates, etc.).

While illustrated and described in conjunction with a helical suture 420, it will be appreciated that other mechanisms may also be suitable for securing rings 412a, 412b within the respective orifices of the mitral valve. For example, a series of hooks and loops or any other mechanism could alternative be used for securing rings 412a, 412b in place.

Figure 32A:
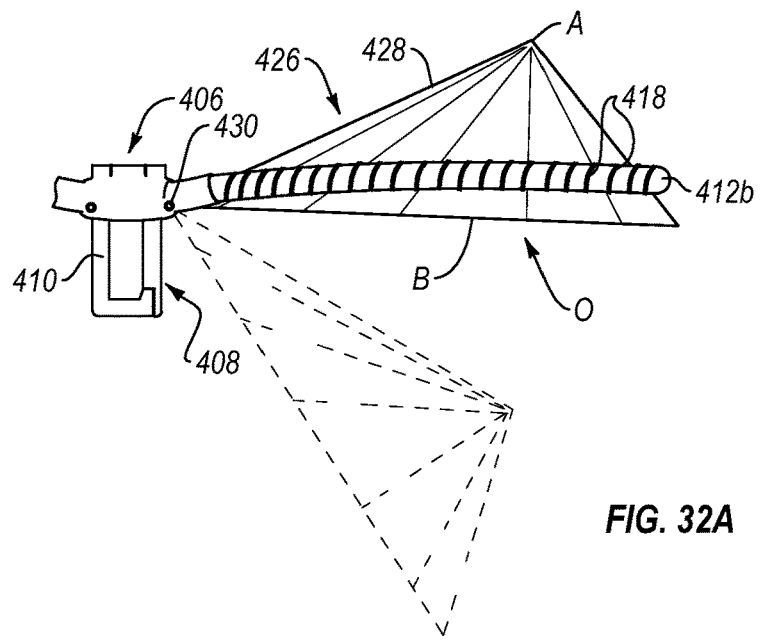
FIG. 32A illustrates a schematic view of an exemplary trap door valve hingedly secured to the anchoring and manifold assembly of the valve device.
Figure 32B:
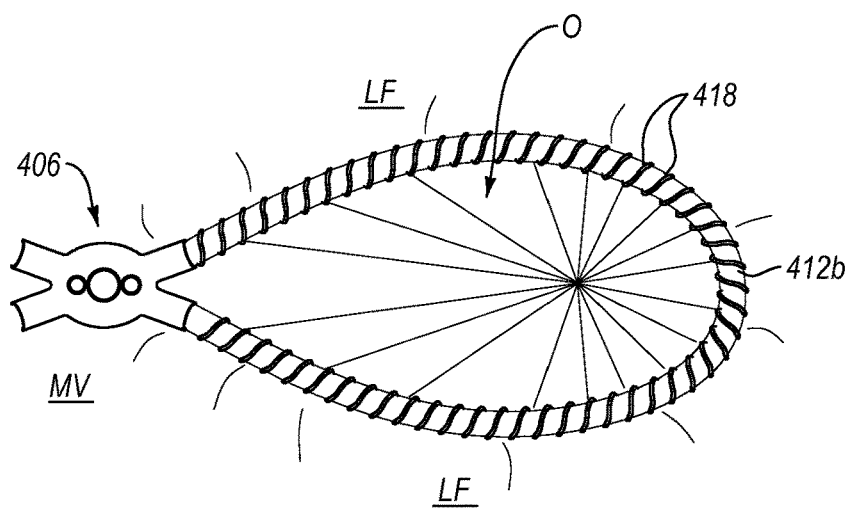
FIG. 32B illustrates a schematic view of the trap door valve of FIG. 32A from the left atrium (i.e., top looking down), with the trap door body of the valve in a closed position, sealed against the anchoring ring.
Figure 32C:
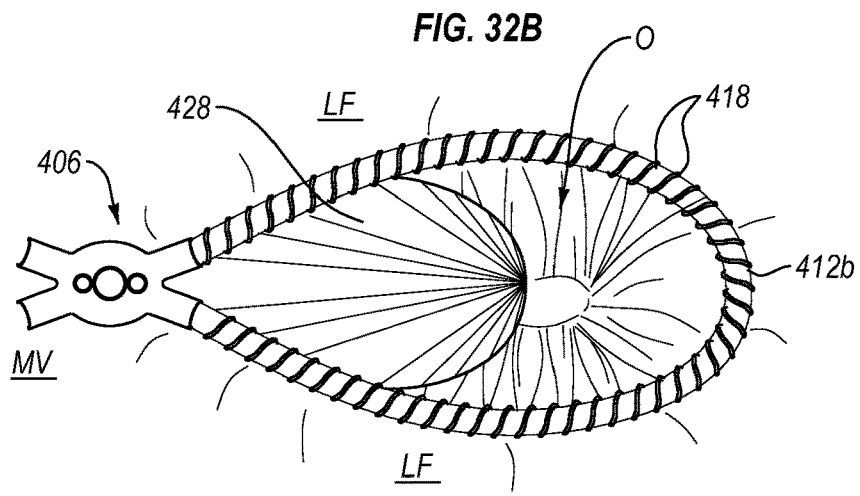
FIG. 32C illustrates a schematic view of the trap door valve of FIGS. 32A-32B from the left atrium (i.e., looking top down), with the trap door body of the valve in an open position.

Once the hardenable polymer or other hardenable material is delivered into rings 412a, 412b using lines 416a, 416b and manifold 407, the trap door valves may be deployed and device 400 may be separated from the delivery catheter. A deployment actuator (e.g., mandril) 425 may be rotated or otherwise manipulated (e.g., through a handle at a proximal end of catheters 402, 404) to disengage lines 416a, 416b, and actuator 425 from the remainder of device 400. FIGS. 32A-33 show device 400 once these structures have been disengaged from the remainder of device 400, which remains within the mitral valve of the heart of the patient.

Because each double orifice valve of any given patient may be of a somewhat different shape, size, and geometry, the valve device advantageously may be capable of opening and closing tightly during the cardiac cycle, regardless of sizing. Trap door valve 426 of valve device 400 may be so configured. As seen in FIG. 32A, trap door valve 426 may be hingedly secured (e.g., via hinge 430) to anchoring and manifold assembly 406, to ring 412b, or to both. In the illustrated configuration, hinge 430 is disposed in the A2/P2 region of the mitral valve (e.g., adjacent basket 408 or other latching or grasping mechanism), once installed. Such a trap door valve may include a trap door body 428 that during the systole portion of the cardiac cycle, selectively seals against the expandable anchoring ring 412b that extends about the annular perimeter of the orifice O of the mitral valve MV. During the diastole portion of the cardiac cycle, trap door body 428 selectively unseals relative to expandable anchoring ring 412a or 412b so as to open orifice O of mitral valve MV.

Such opening and closing of trap door valve 426 may be achieved automatically, in response to relative fluid (e.g., blood) pressures present in the ventricle and atrium. For example, when pressure within the ventricle is higher than that within the atrium, trap door body 428 will be pushed upwards, as illustrated in FIGS. 32A-32B, closing orifice O, and providing an effective seal of orifice about ring 412b. When pressure within the atrium is higher than that within the ventricle, trap door body 428 will be pressed downwards, opening orifice O, as shown in FIG. 32C (and in phantom in FIG. 32A).

Figure 32D:
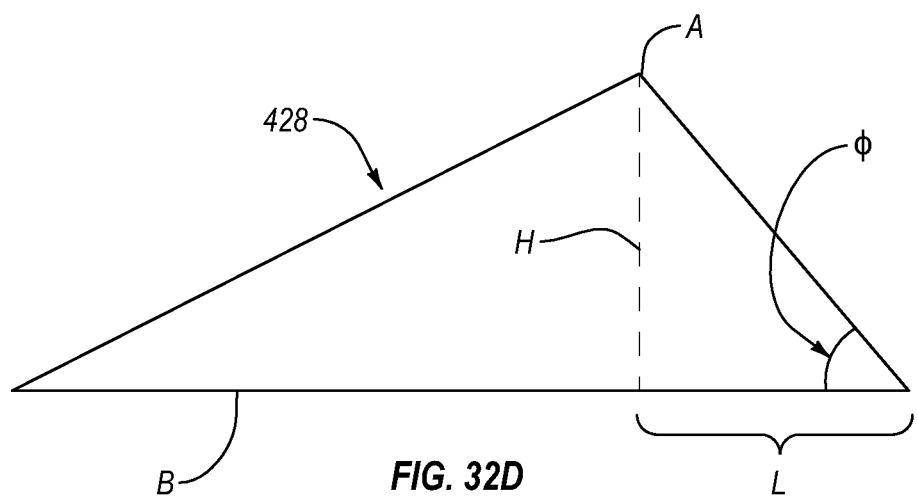
FIG. 32D illustrates a schematic side view of the trap door valve of FIGS. 32A-32B from the left atrium (i.e., looking top down), with the trap door body of the valve in an open position.
Figure 33:
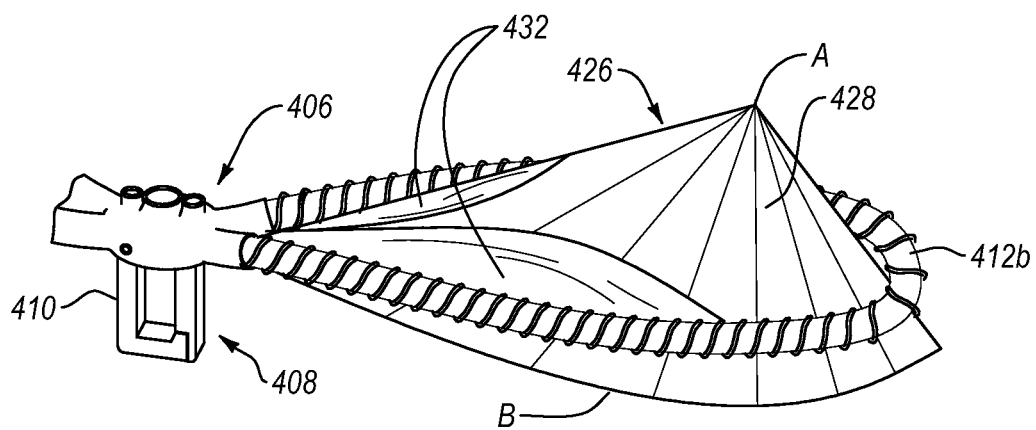
FIG. 33 illustrates a schematic view of an exemplary device similar to the view of FIG. 32B, showing a sealing flap attached to the anchoring ring for aiding in providing a seal between the anchoring ring and the trap door body.

Trap door body 428 may be configured with a generally triangular cross-sectioned cone-shape, as seen in FIG. 32A and FIG. 32D. The height H from apex A to base B and length L at base B (above apex A) to the edge of the trap door body 428 may be such that $H=L \cdot \tan(\Phi)$. The extension of ring 412b determines where the ring touches the trap door body 428 so as to shut the valve 426. In this way, the valve 426 has sufficient flexibility or versatility to shut at a wide range of orifice sizes as the triangular or cone shaped configuration self-adjusts the dimensions of H, L and angle $\Phi$ such that $H=L \cdot \tan(\Phi)$. Less required ring extension will thus be associated with a lower rise of the apex (i.e., lower height H), and correspondingly decreased angle $\Phi$.

As shown in FIGS. 32A and 32D, the base B of the cone-shaped trap door body 428 may reside below (i.e., distal, towards the ventricle side) the tubular ring 412b. The base of body 428 may be substantially parallel to, and just distal to or below the same plane as the ring 412b when in a closed position, and hingedly rotates downward (FIG. 32A, 32C) when the valve opens. The apex A of the cone shaped trap door body 428 faces proximally, toward the atrial side of the heart. During the diastolic portion of the cardiac cycle, the cone-shaped trap door body 428 lowers to permit blood to flow from the atrium to the ventricle. During the systolic portion of the cardiac cycle, the cone shaped structure 428 is raised to prevent blood from passing back into the atrium.

The shape of the perimeter of the cone-shaped trap door body 428 near its base B approximates the shape of the orifice that is reinforced by the tubular ring 412b (see FIG. 32B). The dimensions of the perimeter of base B are at least as large as those of the orifice defined by ring 412b (i.e., measured as the inside edges of ring 412b) in order to close the orifice and prevent or minimize blood flow between ring 412 and cone shaped trap door body 428 when in a closed position, as seen in FIG. 32A.

Thus, trap door body 428 may include a geometry that allows a given size trap door body 428 to close and seal around a variety of differently sized orifice O perimeters surrounded by the expandable anchoring ring (e.g., 412b) expanded therein.

While not illustrated in FIGS. 32A-32D for purposes of clearly showing the trap door valve 426, each side of device 400 may further include a sealing flap 432, as shown in FIG. 33. Such a flap 432 may be attached to tubular rings 412a, 412b. Flap 432 aids in providing an effective seal between trap door body 428 and ring 412b. Flap 432 may extend outwardly from ends 414 of ring 412b, where ends 414 of ring 412 couple into assembly 406. Flaps 432 may extend from ends 414 at least partially along both legs of ring 412b. In an embodiment, as shown, flap 432 may terminate shy of the looped, far end of ring 412b opposite ends 414. It will be appreciated that in a double orifice valve device, opposite ring 412a may similarly include the features shown and described above in detail relative to ring 412b (e.g., trap door valve 426, trap door body 428, flap 432, etc.).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orifice valve device for attachment to a mitral valve defining at least two orifices, the device comprising:
   an anchoring and manifold assembly coupleable to a delivery catheter;
   a peripheral ring anchoring system fluidly communicating with and secured to the anchoring and manifold assembly, the peripheral ring anchoring system including:
   two expandable anchoring rings, wherein each expandable anchoring ring can be expanded within a respective orifice of the mitral valve so as to surround a perimeter of the respective orifice and form a corresponding opening, the two expandable anchoring rings being in fluid communication and disposed on opposite sides of the anchoring and manifold assembly whereby the anchoring and manifold assembly forms a portion of a perimeter of each of the corresponding openings;
   two helical sutures, each of the two helical sutures being helically disposeable about a respective one of the two expandable anchoring rings to secure the respective one of the two expandable anchoring rings to leaflet tissue around the perimeter of the respective orifice of the mitral valve; and two trap door valves, each trap door valve hingedly secured within a respective opening formed by the peripheral ring anchoring system, each trap door valve comprising:

a trap door body that selectively seals against a respective one of the two expandable anchoring rings extending around the perimeter of a respective orifice of the mitral valve during a systole portion of a cardiac cycle, the trap door body selectively unsealing relative to the one of the two expandable anchoring rings so as to open the corresponding opening and thus the respective orifice of the mitral valve, during a diastole portion of the cardiac cycle.

2. The device of claim 1, wherein the anchoring and manifold assembly comprises a basket including a selectively movable arm for opening and closing the basket so as to selectively capture at least a portion of a fixation device that is attached to the mitral valve to anchor the valve device to the fixation device when at least a portion of the fixation device is captured within the basket.

3. The device of claim 1, wherein the peripheral ring anchoring system further comprises two helical suture conduits, each attached to a respective one of the two expandable anchoring rings, each of the two helical suture conduits being discontinuous so as to extend about a portion of a perimeter of the respective expandable anchoring ring that is not disposed adjacent to the leaflet tissue of the mitral valve, such that each of the two helical sutures can be introduced into a first section of the respective one of the two discontinuous helical suture conduits so as to extend through the first section of the respective helical suture conduit, through leaflet tissue adjacent a distal end of the first section of the respective helical suture conduit, and into an adjacent second section of the discontinuous respective helical suture conduit.

4. The device of claim 1, wherein each trap door valve further comprises a sealing flap attached to the respective one of the two expandable anchoring rings for aiding in providing a seal between the respective one of the two expandable anchoring rings and the trap door body.

5. The device of claim 1, wherein the anchoring and manifold assembly comprises manifold and fluid distribution lines, the manifold and distribution lines being in fluid communication with the two expandable anchoring rings to allow introduction of fluids from the delivery catheter, through the distribution lines into the manifold, and into the two expandable anchoring rings.

6. The device of claim 1, wherein each trap door body includes a geometry that allows a given size trap door body to close and seal around a variety of differently sized orifice perimeters with the respective one of two expandable anchoring rings expanded therein.

7. A double orifice valve device for attachment to an edge-to-edge repaired mitral valve defining at least two orifices, the device comprising:

an anchoring and manifold assembly coupleable to a delivery catheter;

a peripheral ring anchoring system secured to the anchoring and manifold assembly, the peripheral ring anchoring system including:

a pair of expandable anchoring rings, wherein each expandable anchoring ring can be expanded within a respective orifice of the mitral valve so as to surround a perimeter of the respective orifice to form an opening similar to the respective orifice defined by the edge-to-edge repaired mitral valve;

a helical suture helically disposeable about the expandable anchoring rings to secure the expandable anchoring rings to leaflet tissue around the perimeters of the respective orifices of the mitral valve; and a pair of trap door valves hingedly secured to at least one of the anchoring and manifold assembly, or the peripheral ring anchoring system, each trap door valve including:

a trap door body that selectively seals against a respective one of the expandable anchoring rings extending around the perimeter of a respective orifice of the mitral valve during a systole portion of a cardiac cycle, the trap door body selectively unsealing relative to the respective expandable anchoring ring so as to open the orifice of the mitral valve during a diastole portion of the cardiac cycle.

8. The device of claim 7, wherein the peripheral ring anchoring system further comprises two helical suture conduits, each attached to a respective one of the two expandable anchoring rings, each of the two helical suture conduits being discontinuous so as to extend about a portion of a perimeter of the respective anchoring ring that is not disposed adjacent to the leaflet tissue of the mitral valve, such that each of the two helical sutures can be introduced into a first section of the respective one of the two discontinuous helical suture conduits so as to extend through the first section of the respective helical suture conduit, through leaflet tissue adjacent a distal end of the first section of the respective helical suture conduit, and into an adjacent second section of the discontinuous respective helical suture conduit.

9. The device of claim 7, wherein each trap door valve further comprises a sealing flap attached to the respective expandable anchoring ring for aiding in providing a seal between the respective expandable anchoring ring and the respective trap door body.

10. The device of claim 7, wherein the anchoring and manifold assembly comprises a basket including a selectively movable arm for opening and closing the basket so as to selectively capture at least a portion of a fixation device that is attached to the mitral valve to anchor the valve device to at least a portion of the fixation device when the fixation device is captured within the basket of the anchoring and manifold assembly.

11. The device of claim 7, wherein the anchoring and manifold assembly comprises manifold and fluid distribution lines, the manifold and distribution lines being in fluid communication with the expandable anchoring rings to allow introduction of fluids from the delivery catheter, through the distribution lines into the manifold, and into the expandable anchoring rings.

12. A method for replacing a mitral valve with a mitral orifice valve device while preserving existing valvular and sub-valvular apparatus of the mitral valve, the method comprising:

delivering a mitral orifice valve device into a heart of a patient, the mitral orifice valve device being delivered through a delivery catheter in a minimally invasive endovascular procedure;

anchoring the mitral orifice valve device to an edge-to-edge repaired mitral valve defining two orifices or to a fixation device that is attached to the mitral valve as part of the edge-to-edge mitral valve repair;

expanding two expandable anchoring rings of the mitral orifice valve device, wherein each expandable anchoring ring is expanded within a respective orifice of the mitral valve so that the expandable anchoring ring surrounds an annular perimeter of each respective orifice and forms a corresponding opening similar to the respective orifice defined by the mitral valve;

securing each expandable anchoring ring to leaflet tissue around the perimeter of each respective orifice with a helical suture;

deploying two trap door valves of the mitral orifice valve device, wherein each trap door valve selectively seals against one of the two expandable anchoring rings extending around the perimeter of one of the two orifices, so as to close the respective orifice of the mitral valve during a systole portion of a cardiac cycle, each trap door valve selectively unsealing against the respective one of the two expandable anchoring rings so as to open the respective orifice of the mitral valve during a diastole portion of the cardiac cycle.

13. The method of claim 12, the method further comprising expanding the orifices serially, one orifice at a time, so as to not completely block diastolic filling of a left ventricle.

14. The method of claim 12, the valve device further comprising a sealing flap attached to the respective one of the two expandable anchoring rings for aiding in providing the seal between the respective one of the two expandable anchoring rings and the trap door body during the systole portion of the cardiac cycle.

15. The method of claim 12, wherein the valve device is anchored to the fixation device that is attached to A2 and P2 regions of the mitral valve, so that the fixation device provides the mitral valve with an edge-to-edge or bow tie type repair.

16. The method of claim 15, wherein the mitral orifice valve device further comprises a basket including a selectively movable arm for opening and closing the basket, the method further comprising capturing at least a portion of the fixation device within the basket of the mitral orifice valve device to anchor the mitral orifice valve device to the fixation device.

17. The method of claim 12, wherein the mitral orifice valve device further comprises a manifold and fluid delivery lines for delivering a fluid into the two expandable anchoring rings, the method further comprising delivering a hardenable fluid into the two expandable anchoring rings and allowing the hardenable fluid to harden once the two expandable anchoring rings are secured to the leaflet tissue around the perimeter of the orifice.

18. The method of claim 17, wherein the hardenable fluid comprises a hardenable polymer.

19. The method of claim 17, further comprising delivering a saline solution through the manifold and fluid delivery lines into the two expandable anchoring rings before delivery of the hardenable fluid into the two expandable anchoring rings, during expansion of the two expandable anchoring rings within the orifice of the mitral valve, before securing the two expandable anchoring rings to leaflet tissue around the perimeter of each of the two orifices with a suture.

* * * * *